(12) United States Patent
Straubinger et al.

(10) Patent No.: US 10,307,251 B2
(45) Date of Patent: Jun. 4, 2019

(54) CATHETER SYSTEM FOR INTRODUCING AN EXPANDABLE STENT INTO THE BODY OF A PATIENT

(71) Applicant: JENAVALVE TECHNOLOGY, INC., Irvine, CA (US)

(72) Inventors: Helmut Straubinger, Aschheim (DE); Arnulf Mayer, Markt Schwaben (DE); Johannes Jung, Pforzheim-Huchenfeld (DE)

(73) Assignee: Jenavalve Technology, Inc., Irvine, CA (US)

( * ) Notice: Subject to any disclaimer, the term of this patent is extended or adjusted under 35 U.S.C. 154(b) by 312 days.

(21) Appl. No.: 15/407,560

(22) Filed: Jan. 17, 2017

(65) Prior Publication Data

US 2017/0156858 A1 Jun. 8, 2017

Related U.S. Application Data

(63) Continuation of application No. 13/698,910, filed as application No. PCT/EP2011/002524 on May 20, (Continued)

(30) Foreign Application Priority Data

May 20, 2010 (EP) .................................... 10163478

(51) Int. Cl.
*A61F 2/24* (2006.01)
*A61F 2/966* (2013.01)
*A61F 2/95* (2013.01)

(52) U.S. Cl.
CPC .......... *A61F 2/2436* (2013.01); *A61F 2/2418* (2013.01); *A61F 2/2433* (2013.01);
(Continued)

(58) Field of Classification Search
CPC ........ A61F 2/2436; A61F 2/2418; A61F 2/95; A61F 2/966; A61F 2/958; A61F 2/2427;
(Continued)

(56) References Cited

U.S. PATENT DOCUMENTS

| | | |
|---|---|---|
| 4,502,488 A | 3/1985 | DeGironimo et al. |
| 4,665,918 A | 5/1987 | Garza et al. |

(Continued)

FOREIGN PATENT DOCUMENTS

| | | |
|---|---|---|
| AU | 2006308187 A1 | 5/2007 |
| AU | 2006310681 A1 | 5/2007 |

(Continued)

OTHER PUBLICATIONS

Aortenklappenbioprothese erfolgreich in der Entwicklung, May 16, 2003 (1 page).

(Continued)

*Primary Examiner* — Robert A Lynch
*Assistant Examiner* — Mohamed G Gabr
(74) *Attorney, Agent, or Firm* — Bookoff McAndrews, PLLC

(57) ABSTRACT

This disclosure relates to a catheter system for introducing a heart valve stent into the body of a patient. The catheter system includes a catheter tip having a seat portion for accommodating the stent in its collapsed state and a stent holder for releasably fixing the stent, wherein the seat portion is constituted by a first sleeve and a second sleeve, said sleeves being moveable relative to each other and relative to the stent holder, and a catheter shaft for connecting the catheter tip to a handle.

20 Claims, 13 Drawing Sheets

Figure 1:
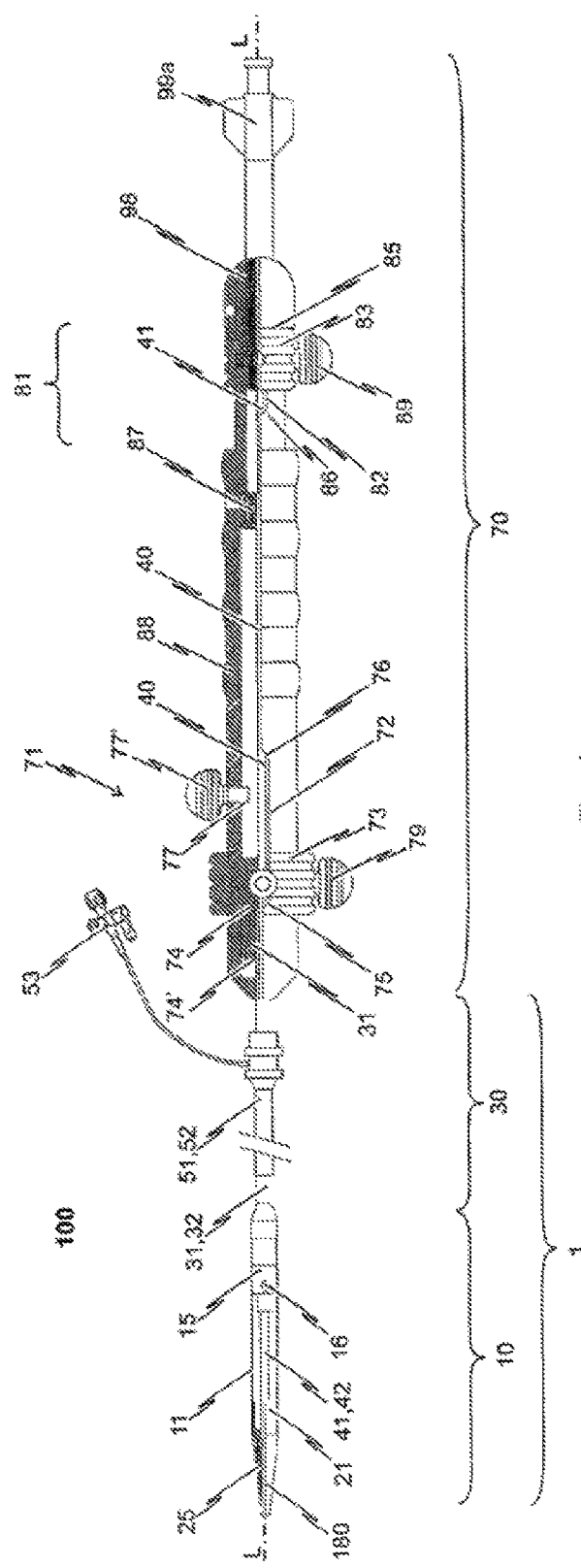

Related U.S. Application Data 2011, now Pat. No. 9,597,182, which is a continuation-in-part of application No. 12/801,090, filed on May 20, 2010.

(52) U.S. Cl.
CPC ...... *A61F 2/966* (2013.01); *A61F 2002/9505* (2013.01); *A61F 2002/9517* (2013.01); *A61F 2002/9665* (2013.01); *A61F 2210/0014* (2013.01)

(58) Field of Classification Search
CPC .. A61F 2/97; A61F 2/2433; A61F 2002/9517; A61F 2002/9665; A61F 2002/9583; A61F 2002/9505; A61F 2002/9534; A61F 2210/0014; A61F 2220/0016
See application file for complete search history.

(56) References Cited

U.S. PATENT DOCUMENTS

| | | |
|---|---|---|
| 4,922,905 A | 5/1990 | Strecker |
| 4,950,227 A | 8/1990 | Savin et al. |
| 5,002,566 A | 3/1991 | Carpentier et al. |
| 5,061,277 A | 10/1991 | Carpentier et al. |
| 5,094,661 A | 3/1992 | Levy et al. |
| 5,104,407 A | 4/1992 | Lam et al. |
| 5,197,979 A | 3/1993 | Quintero et al. |
| 5,201,757 A | 4/1993 | Heyn et al. |
| 5,211,183 A | 5/1993 | Wilson |
| 5,279,612 A | 1/1994 | Eberhardt |
| 5,332,402 A | 7/1994 | Teitelbaum |
| 5,336,258 A | 8/1994 | Quintero et al. |
| 5,352,240 A | 10/1994 | Ross |
| 5,368,608 A | 11/1994 | Levy et al. |
| 5,411,552 A | 5/1995 | Andersen et al. |
| 5,433,723 A | 7/1995 | Lindenberg et al. |
| 5,456,713 A | 10/1995 | Chuter |
| 5,509,930 A | 4/1996 | Love |
| 5,534,007 A | 7/1996 | St. Germain et al. |
| 5,549,666 A | 8/1996 | Hata et al. |
| 5,595,571 A | 1/1997 | Jaffe et al. |
| 5,613,982 A | 3/1997 | Goldstein |
| 5,632,778 A | 5/1997 | Goldstein |
| 5,674,298 A | 10/1997 | Levy et al. |
| 5,679,112 A | 10/1997 | Levy et al. |
| 5,683,451 A | 11/1997 | Lenker et al. |
| 5,690,644 A | 11/1997 | Yurek et al. |
| 5,697,972 A | 12/1997 | Kim et al. |
| 5,713,953 A | 2/1998 | Vallana et al. |
| 5,746,775 A | 5/1998 | Levy et al. |
| 5,755,777 A | 5/1998 | Chuter |
| 5,824,041 A | 10/1998 | Lenker et al. |
| 5,824,080 A | 10/1998 | Lamuraglia |
| 5,840,081 A | 11/1998 | Andersen et al. |
| 5,841,382 A | 11/1998 | Walden et al. |
| 5,843,181 A | 12/1998 | Jaffe et al. |
| 5,876,434 A | 3/1999 | Flomenblit et al. |
| 5,880,242 A | 3/1999 | Hu et al. |
| 5,899,936 A | 5/1999 | Goldstein |
| 5,906,619 A | 5/1999 | Olson et al. |
| 5,928,281 A | 7/1999 | Huynh et al. |
| 5,935,163 A | 8/1999 | Gabbay |
| 5,104,407 B1 | 9/1999 | Lam et al. |
| 6,001,126 A | 12/1999 | Nguyen-Thien-Nhon |
| 5,061,277 B1 | 2/2000 | Carpentier et al. |
| 6,019,777 A | 2/2000 | Mackenzie |
| 6,019,778 A | 2/2000 | Wilson et al. |
| 6,077,297 A | 6/2000 | Robinson et al. |
| 6,093,530 A | 7/2000 | McIlroy et al. |
| 6,102,944 A | 8/2000 | Huynh et al. |
| 6,117,169 A | 9/2000 | Moe |
| 6,126,685 A | 10/2000 | Lenker et al. |
| 6,146,415 A | 11/2000 | Fitz |
| 6,168,614 B1 | 1/2001 | Andersen et al. |
| 6,177,514 B1 | 1/2001 | Pathak et al. |
| 6,183,481 B1 | 2/2001 | Lee et al. |
| 6,190,393 B1 | 2/2001 | Bevier et al. |
| 6,200,336 B1 | 3/2001 | Pavcnik et al. |
| 6,214,055 B1 | 4/2001 | Simionescu et al. |
| 6,231,602 B1 | 5/2001 | Carpentier et al. |
| 6,254,564 B1 | 7/2001 | Wilk et al. |
| 6,254,636 B1 | 7/2001 | Peredo |
| 6,276,661 B1 | 8/2001 | Laird |
| 6,283,995 B1 | 9/2001 | Moe et al. |
| 6,287,338 B1 | 9/2001 | Sarnowski et al. |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,350,278 B1 | 2/2002 | Lenker et al. |
| 6,379,365 B1 | 4/2002 | Diaz |
| 6,379,740 B1 | 4/2002 | Rinaldi et al. |
| 6,391,538 B1 | 5/2002 | Vyavahare et al. |
| 6,425,916 B1 | 7/2002 | Garrison et al. |
| 6,454,799 B1 | 9/2002 | Schreck |
| 6,471,723 B1 | 10/2002 | Ashworth et al. |
| 6,475,169 B2 | 11/2002 | Ferrera |
| 6,478,819 B2 | 11/2002 | Moe |
| 6,508,833 B2 | 1/2003 | Pavcnik et al. |
| 6,509,145 B1 | 1/2003 | Torrianni |
| 6,521,179 B1 | 2/2003 | Girardot et al. |
| 6,540,782 B1 | 4/2003 | Snyders |
| 6,558,417 B2 | 5/2003 | Peredo |
| 6,558,418 B2 | 5/2003 | Carpentier et al. |
| 6,562,063 B1 | 5/2003 | Euteneuer et al. |
| 6,572,642 B2 | 6/2003 | Rinaldi et al. |
| 6,582,460 B1 | 6/2003 | Cryer |
| 6,582,462 B1 | 6/2003 | Andersen et al. |
| 6,585,766 B1 | 7/2003 | Huynh et al. |
| 6,613,086 B1 | 9/2003 | Moe et al. |
| 6,623,491 B2 | 9/2003 | Thompson |
| 6,682,559 B2 | 1/2004 | Myers et al. |
| 6,730,118 B2 | 5/2004 | Spenser et al. |
| 6,736,845 B2 | 5/2004 | Marquez et al. |
| 6,767,362 B2 | 7/2004 | Schreck |
| 6,790,230 B2 | 9/2004 | Beyersdorf et al. |
| 6,808,529 B2 | 10/2004 | Fulkerson |
| 6,821,211 B2 | 11/2004 | Otten et al. |
| 6,821,297 B2 | 11/2004 | Snyders |
| 6,824,970 B2 | 11/2004 | Vyavahare et al. |
| 6,830,575 B2 | 12/2004 | Stenzel et al. |
| 6,830,584 B1 | 12/2004 | Seguin |
| 6,849,084 B2 | 2/2005 | Rabkin et al. |
| 6,861,211 B2 | 3/2005 | Levy et al. |
| 6,872,226 B2 | 3/2005 | Cali et al. |
| 6,881,199 B2 | 4/2005 | Wilk et al. |
| 6,893,460 B2 | 5/2005 | Spenser et al. |
| 6,908,481 B2 | 6/2005 | Cribier |
| 6,911,043 B2 | 6/2005 | Myers et al. |
| 6,945,997 B2 | 9/2005 | Huynh et al. |
| 6,974,474 B2 | 12/2005 | Pavcnik et al. |
| 7,014,655 B2 | 3/2006 | Barbarash et al. |
| 7,018,406 B2 | 3/2006 | Seguin et al. |
| 7,037,333 B2 | 5/2006 | Myers et al. |
| 7,050,276 B2 | 5/2006 | Nishiyama |
| 7,078,163 B2 | 7/2006 | Torrianni |
| 7,081,132 B2 | 7/2006 | Cook et al. |
| 7,137,184 B2 | 11/2006 | Schreck et al. |
| 7,141,064 B2 | 11/2006 | Scott et al. |
| 7,163,556 B2 | 1/2007 | Xie et al. |
| 7,189,259 B2 | 3/2007 | Simionescu et al. |
| 7,198,646 B2 | 4/2007 | Figulla et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,264,632 B2 | 9/2007 | Wright et al. |
| 7,318,278 B2 | 1/2008 | Zhang et al. |
| 7,318,998 B2 | 1/2008 | Goldstein et al. |
| 7,322,932 B2 | 1/2008 | Xie et al. |
| 7,323,006 B2 | 1/2008 | Andreas et al. |
| 7,329,278 B2 | 2/2008 | Seguin et al. |
| 7,381,216 B2 | 6/2008 | Buzzard et al. |
| 7,381,218 B2 | 6/2008 | Schreck |
| 7,393,360 B2 | 7/2008 | Spenser et al. |

(56) References Cited

U.S. PATENT DOCUMENTS

| | | |
|---|---|---|
| 7,399,315 B2 | 7/2008 | Iobbi |
| 7,452,371 B2 | 11/2008 | Pavcnik et al. |
| 7,473,275 B2 | 1/2009 | Marquez |
| 7,476,244 B2 | 1/2009 | Buzzard et al. |
| 7,651,519 B2 | 1/2010 | Dittman |
| 7,771,463 B2 | 8/2010 | Ton et al. |
| 7,862,602 B2 | 1/2011 | Licata et al. |
| 7,896,915 B2 | 3/2011 | Guyenot et al. |
| 7,914,575 B2 | 3/2011 | Guyenot et al. |
| 8,083,788 B2 | 12/2011 | Acosta et al. |
| 8,343,136 B2 | 1/2013 | Howat et al. |
| 8,491,650 B2 | 7/2013 | Wiemeyer et al. |
| 8,512,400 B2 | 8/2013 | Tran et al. |
| 8,512,401 B2 | 8/2013 | Murray, III et al. |
| 8,795,305 B2 | 8/2014 | Martin et al. |
| 8,852,272 B2 | 10/2014 | Gross et al. |
| 8,956,383 B2 | 2/2015 | Aklog et al. |
| 9,186,482 B2 | 11/2015 | Dorn |
| 9,301,840 B2 | 4/2016 | Nguyen et al. |
| 2001/0011187 A1 | 8/2001 | Pavcnik et al. |
| 2001/0037141 A1 | 11/2001 | Yee et al. |
| 2001/0039450 A1 | 11/2001 | Pavcnik et al. |
| 2002/0032481 A1 | 3/2002 | Gabbay |
| 2002/0045929 A1 | 4/2002 | Diaz |
| 2002/0055775 A1 | 5/2002 | Carpentier et al. |
| 2002/0120323 A1 | 8/2002 | Thompson et al. |
| 2002/0123790 A1 | 9/2002 | White et al. |
| 2002/0133226 A1 | 9/2002 | Marquez et al. |
| 2002/0193871 A1 | 12/2002 | Beyersdorf et al. |
| 2002/0198594 A1 | 12/2002 | Schreck |
| 2003/0027332 A1 | 2/2003 | Lafrance et al. |
| 2003/0036791 A1 | 2/2003 | Philipp et al. |
| 2003/0036795 A1 | 2/2003 | Andersen et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0114913 A1 | 6/2003 | Spenser et al. |
| 2003/0125795 A1 | 7/2003 | Pavcnik et al. |
| 2003/0139796 A1 | 7/2003 | Sequin et al. |
| 2003/0139803 A1 | 7/2003 | Sequin et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0195620 A1 | 10/2003 | Huynh et al. |
| 2003/0212410 A1 | 11/2003 | Stenzel et al. |
| 2003/0236570 A1 | 12/2003 | Cook et al. |
| 2004/0006380 A1 | 1/2004 | Buck et al. |
| 2004/0039436 A1 | 2/2004 | Spenser et al. |
| 2004/0049262 A1 | 3/2004 | Obermiller et al. |
| 2004/0073289 A1 | 4/2004 | Hartley et al. |
| 2004/0078950 A1 | 4/2004 | Schreck et al. |
| 2004/0117004 A1 | 6/2004 | Osborne et al. |
| 2004/0117009 A1 | 6/2004 | Cali et al. |
| 2004/0148018 A1 | 7/2004 | Carpentier et al. |
| 2004/0153145 A1 | 8/2004 | Simionescu et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0193244 A1 | 9/2004 | Hartley et al. |
| 2004/0210301 A1 | 10/2004 | Obermiller et al. |
| 2004/0210304 A1 | 10/2004 | Seguin et al. |
| 2004/0215317 A1 | 10/2004 | Cummings |
| 2004/0260389 A1 | 12/2004 | Case et al. |
| 2005/0009000 A1 | 1/2005 | Wilhelm et al. |
| 2005/0033220 A1 | 2/2005 | Wilk et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0075725 A1 | 4/2005 | Rowe |
| 2005/0075776 A1 | 4/2005 | Cho |
| 2005/0096726 A1 | 5/2005 | Sequin et al. |
| 2005/0096735 A1 | 5/2005 | Hojeibane et al. |
| 2005/0096736 A1 | 5/2005 | Osse et al. |
| 2005/0098547 A1 | 5/2005 | Cali et al. |
| 2005/0113910 A1 | 5/2005 | Paniagua et al. |
| 2005/0119728 A1 | 6/2005 | Sarac |
| 2005/0119736 A1 | 6/2005 | Zilla et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137697 A1 | 6/2005 | Salahieh et al. |
| 2005/0137698 A1 | 6/2005 | Salahieh et al. |
| 2005/0137702 A1 | 6/2005 | Haug et al. |
| 2005/0143804 A1 | 6/2005 | Haverkost |
| 2005/0143807 A1 | 6/2005 | Pavcnik et al. |
| 2005/0149166 A1 | 7/2005 | Schaeffer et al. |
| 2005/0150775 A1 | 7/2005 | Zhang et al. |
| 2005/0171597 A1 | 8/2005 | Boatman et al. |
| 2005/0171598 A1 | 8/2005 | Schaeffer |
| 2005/0192665 A1 | 9/2005 | Spenser et al. |
| 2005/0197695 A1 | 9/2005 | Stacchino et al. |
| 2005/0222664 A1 | 10/2005 | Parker |
| 2005/0222668 A1 | 10/2005 | Schaeffer et al. |
| 2005/0234546 A1 | 10/2005 | Nugent et al. |
| 2005/0267560 A1 | 12/2005 | Bates |
| 2006/0009842 A1 | 1/2006 | Huynh et al. |
| 2006/0025857 A1 | 2/2006 | Bergheim et al. |
| 2006/0047343 A1 | 3/2006 | Oviatt et al. |
| 2006/0058864 A1 | 3/2006 | Schaeffer et al. |
| 2006/0058872 A1 | 3/2006 | Salahieh et al. |
| 2006/0074477 A1 | 4/2006 | Berthiaume et al. |
| 2006/0074484 A1 | 4/2006 | Huber |
| 2006/0111770 A1 | 5/2006 | Pavcnik et al. |
| 2006/0142846 A1 | 6/2006 | Pavcnik et al. |
| 2006/0149360 A1 | 7/2006 | Schwammenthal et al. |
| 2006/0155366 A1 | 7/2006 | LaDuca et al. |
| 2006/0167543 A1 | 7/2006 | Bailey et al. |
| 2006/0178740 A1 | 8/2006 | Stacchino et al. |
| 2006/0193885 A1 | 8/2006 | Neethling et al. |
| 2006/0210597 A1 | 9/2006 | Hiles |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0246584 A1 | 11/2006 | Covelli |
| 2006/0253191 A1 | 11/2006 | Salahieh et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276873 A1 | 12/2006 | Sato |
| 2006/0276874 A1 | 12/2006 | Wilson et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0020248 A1 | 1/2007 | Everaerts et al. |
| 2007/0021826 A1 | 1/2007 | Case et al. |
| 2007/0027535 A1 | 2/2007 | Purdy, Jr. et al. |
| 2007/0038291 A1 | 2/2007 | Case et al. |
| 2007/0038295 A1 | 2/2007 | Case et al. |
| 2007/0043435 A1 | 2/2007 | Seguin et al. |
| 2007/0050014 A1 | 3/2007 | Johnson |
| 2007/0078504 A1 | 4/2007 | Mialhe |
| 2007/0088431 A1 | 4/2007 | Bourang et al. |
| 2007/0093887 A1 | 4/2007 | Case et al. |
| 2007/0100435 A1 | 5/2007 | Case et al. |
| 2007/0100440 A1 | 5/2007 | Figulla et al. |
| 2007/0112422 A1 | 5/2007 | Dehdashtian |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0162103 A1 | 7/2007 | Case et al. |
| 2007/0173932 A1 | 7/2007 | Cali et al. |
| 2007/0179592 A1 | 8/2007 | Schaeffer |
| 2007/0185565 A1 | 8/2007 | Schwammenthal et al. |
| 2007/0198078 A1 | 8/2007 | Berra et al. |
| 2007/0203576 A1 | 8/2007 | Lee et al. |

(56) References Cited

U.S. PATENT DOCUMENTS

| | | |
|---|---|---|
| 2007/0213813 A1 | 9/2007 | Von Segesser et al. |
| 2007/0233222 A1 | 10/2007 | Roeder et al. |
| 2007/0239271 A1 | 10/2007 | Nguyen |
| 2007/0244551 A1 | 10/2007 | Stobie |
| 2007/0255390 A1 | 11/2007 | Ducke et al. |
| 2007/0260301 A1 | 11/2007 | Chuter et al. |
| 2007/0260327 A1 | 11/2007 | Case et al. |
| 2007/0288087 A1 | 12/2007 | Fearnot et al. |
| 2008/0004688 A1 | 1/2008 | Spenser et al. |
| 2008/0021546 A1 | 1/2008 | Patz et al. |
| 2008/0033534 A1 | 2/2008 | Cook et al. |
| 2008/0065011 A1 | 3/2008 | Marchand et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077236 A1 | 3/2008 | Letac et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0133003 A1 | 6/2008 | Seguin et al. |
| 2008/0140189 A1 | 6/2008 | Nguyen et al. |
| 2008/0147182 A1 | 6/2008 | Righini et al. |
| 2008/0154355 A1 | 6/2008 | Benichou et al. |
| 2008/0255660 A1 | 6/2008 | Straubinger et al. |
| 2008/0200977 A1 | 8/2008 | Paul et al. |
| 2008/0215143 A1 | 9/2008 | Seguin |
| 2008/0255661 A1 | 10/2008 | Straubinger et al. |
| 2008/0262590 A1 | 10/2008 | Murray |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2009/0005863 A1 | 1/2009 | Goetz et al. |
| 2009/0093876 A1 | 4/2009 | Nitzan et al. |
| 2009/0216313 A1 | 8/2009 | Straubinger et al. |
| 2009/0222076 A1 | 9/2009 | Figulla et al. |
| 2010/0057051 A1 | 3/2010 | Howat et al. |
| 2010/0100167 A1 | 4/2010 | Bortlein et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2011/0257733 A1 | 10/2011 | Dwork |
| 2011/0288626 A1 | 11/2011 | Straubinger et al. |
| 2012/0185030 A1 | 7/2012 | Igaki et al. |
| 2012/0316637 A1 | 12/2012 | Holm et al. |
| 2013/0274870 A1 | 10/2013 | Lombardi et al. |
| 2015/0127092 A1 | 5/2015 | Straubinger et al. |

FOREIGN PATENT DOCUMENTS

| | | |
|---|---|---|
| CA | 2436258 A1 | 1/2005 |
| CA | 2595233 A1 | 7/2006 |
| CA | 2627555 | 5/2007 |
| DE | 19546692 A1 | 6/1997 |
| DE | 20003874 U1 | 6/2000 |
| DE | 19857887 A1 | 7/2000 |
| DE | 10010073 A1 | 9/2001 |
| DE | 10010074 A1 | 10/2001 |
| DE | 101 21 210 A1 | 11/2002 |
| DE | 19546692 C2 | 11/2002 |
| DE | 10301026 A1 | 2/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10010073 B4 | 12/2005 |
| DE | 10 2005 051 849 | 5/2007 |
| DE | 10 2005 052628 A1 | 5/2007 |
| DE | 20 2007 005 491 U1 | 7/2007 |
| EP | 0084395 A1 | 7/1983 |
| EP | 0402036 B1 | 12/1990 |
| EP | 0402176 B1 | 12/1990 |
| EP | 0458877 B1 | 4/1991 |
| EP | 0515324 A1 | 11/1992 |
| EP | 0547135 B1 | 6/1993 |
| EP | 0 592 410 B1 | 10/1995 |
| EP | 0 592 410 B1 | 11/1995 |
| EP | 0729364 B1 | 9/1996 |
| EP | 0756498 B1 | 5/1997 |
| EP | 0778775 B1 | 6/1997 |
| EP | 0928615 A1 | 7/1999 |
| EP | 0986348 B1 | 3/2000 |
| EP | 1 251 805 B1 | 10/2000 |
| EP | 1041942 B1 | 10/2000 |
| EP | 1041943 B1 | 10/2000 |
| EP | 1117446 B1 | 7/2001 |
| EP | 1 233 731 B1 | 5/2002 |
| EP | 1206179 B1 | 5/2002 |
| EP | 1251804 B1 | 10/2002 |
| EP | 0 971 649 B1 | 12/2002 |
| EP | 1281357 A2 | 2/2003 |
| EP | 1281375 A2 | 2/2003 |
| EP | 1 017 868 B1 | 9/2003 |
| EP | 1354569 A1 | 10/2003 |
| EP | 1452153 A1 | 9/2004 |
| EP | 0987998 B1 | 10/2004 |
| EP | 1 087 727 B1 | 11/2004 |
| EP | 1499366 B1 | 1/2005 |
| EP | 1 253 875 B1 | 4/2005 |
| EP | 1 251 803 B1 | 6/2005 |
| EP | 1469797 B1 | 11/2005 |
| EP | 1690515 A1 | 8/2006 |
| EP | 1 255 510 B1 | 3/2007 |
| EP | 1112042 B1 | 11/2007 |
| EP | 1878407 A1 | 1/2008 |
| EP | 1886649 A2 | 2/2008 |
| EP | 1 900 343 A2 | 3/2008 |
| EP | 1259195 B1 | 10/2008 |
| EP | 1980220 A1 | 10/2008 |
| EP | 1994913 A2 | 11/2008 |
| EP | 2 000 115 A2 | 12/2008 |
| FR | 2828263 A1 | 2/2003 |
| GB | 2433700 A | 7/2007 |
| GB | 2440809 A | 2/2008 |
| JP | 64-49571 A | 2/1989 |
| JP | 2003-523262 | 8/2003 |
| JP | 2003-524504 | 8/2003 |
| JP | 2005-118585 | 5/2005 |
| JP | 2007-296375 | 11/2007 |
| JP | 2008-539305 | 11/2008 |
| WO | WO-90/09102 | 8/1990 |
| WO | WO 95/11055 A1 | 4/1995 |
| WO | WO-95/24873 | 9/1995 |
| WO | WO-95/28183 | 10/1995 |
| WO | WO-96/13227 | 5/1996 |
| WO | WO-97/32615 | 9/1997 |
| WO | WO-98/43556 | 10/1998 |
| WO | WO-98/46165 | 10/1998 |
| WO | WO-99/37337 | 7/1999 |
| WO | WO 99/53987 | 10/1999 |
| WO | WO-99/66863 | 12/1999 |
| WO | WO 00/02503 | 1/2000 |
| WO | WO 00/15148 | 3/2000 |
| WO | WO-00/18445 | 4/2000 |
| WO | WO 2000/25702 A1 | 5/2000 |
| WO | WO 00/47139 A1 | 8/2000 |
| WO | WO-00/53125 | 9/2000 |
| WO | WO-00/62714 | 10/2000 |
| WO | WO-01/10209 A1 | 2/2001 |
| WO | WO 2001/35870 A1 | 5/2001 |
| WO | WO-01/41679 A1 | 6/2001 |
| WO | WO-01/51104 A1 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO 2002/36048 A1 | 5/2002 |
| WO | WO-02/058745 A1 | 8/2002 |
| WO | WO-02/100301 A1 | 12/2002 |

(56) References Cited

FOREIGN PATENT DOCUMENTS

| | | |
|---|---|---|
| WO | WO-02/102286 A1 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03/009785 A1 | 2/2003 |
| WO | WO 03/013239 | 2/2003 |
| WO | WO 2003/011195 A2 | 2/2003 |
| WO | WO 03/028592 A1 | 4/2003 |
| WO | WO 03/047468 A1 | 6/2003 |
| WO | WO-03/079928 A2 | 10/2003 |
| WO | WO 2003/096935 A1 | 11/2003 |
| WO | WO 2004/004597 A2 | 1/2004 |
| WO | WO 2004/016200 A1 | 2/2004 |
| WO | WO 2004/016201 A2 | 2/2004 |
| WO | WO 2004/019825 A1 | 3/2004 |
| WO | WO-2004/026117 A2 | 4/2004 |
| WO | WO 2004/026173 A1 | 4/2004 |
| WO | WO 2004/028399 A2 | 4/2004 |
| WO | WO 2004/043301 A1 | 5/2004 |
| WO | WO 2004/082527 A2 | 9/2004 |
| WO | WO 2004/082528 A2 | 9/2004 |
| WO | WO 2004/096100 A1 | 11/2004 |
| WO | WO 2005/021063 A2 | 3/2005 |
| WO | WO 2005/034812 A1 | 4/2005 |
| WO | WO 2005/062980 A1 | 7/2005 |
| WO | WO 2005/062980 A2 | 7/2005 |
| WO | WO 2005/070343 A1 | 8/2005 |
| WO | WO-2005/072654 A1 | 8/2005 |
| WO | WO 2006/066327 | 6/2006 |
| WO | WO-2006/066327 A1 | 6/2006 |
| WO | WO 2006/076890 | 7/2006 |
| WO | WO 2006/089517 A1 | 8/2006 |
| WO | WO-2006/102063 A2 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006/132948 A1 | 12/2006 |
| WO | WO 2006/133959 A1 | 12/2006 |
| WO | WO 2007/047488 A2 | 4/2007 |
| WO | WO 2007/047945 A2 | 4/2007 |
| WO | WO-2007/048529 A1 | 5/2007 |
| WO | WO 2007/051620 A1 | 5/2007 |
| WO | WO 2007/059252 A1 | 5/2007 |
| WO | WO-2007/071436 A2 | 6/2007 |
| WO | WO 2007/098232 A2 | 8/2007 |
| WO | WO 2007/120543 A1 | 10/2007 |
| WO | WO-2008/028569 A1 | 3/2008 |
| WO | WO 2008/035337 A2 | 3/2008 |
| WO | WO 2008/045949 | 4/2008 |
| WO | WO 2008/070797 A2 | 6/2008 |
| WO | WO 2008/079962 A1 | 7/2008 |
| WO | WO 2008/098191 A2 | 8/2008 |
| WO | WO 2008/101083 A2 | 8/2008 |
| WO | WO 2008/125153 A1 | 10/2008 |
| WO | WO 2008/138584 A1 | 11/2008 |
| WO | WO-2008138584 A1 * 11/2008 ........... A61F 2/2436 |  |
| WO | WO 2008/150529 A1 | 12/2008 |
| WO | WO 2011/102968 A1 | 8/2011 |

OTHER PUBLICATIONS

English translation of Aortenklappenbioprothese erfolgreich in der Entwicklung (2 pages).
Screen shots from http://www.fraunhofer.de/presse/filme/2006/index.jsp, 2006 (2 pages).
Liang, Ma, et al., "Double-crowned valved stents for off-pump mitral valve replacement," *Eur. J. Cardio-Thoracic Surgery*, vol. 28, pp. 194-198 (2005) (5 pages).
Huber, Christoph H., et al. "Direct Access Valve Replacement (DAVR)—are we entering a new era in cardiac surgery?" *Eur. J. Cardio-Thoracic Surgery*, vol. 29, pp. 380-385 (2006) (6 pages).
English translation of DE 19546692 A1 (3 pages).
English translation of EP 1469797 B1 (15 pages).
File history for German Patent DE 195 46 692 filed Dec. 14, 1995 and patented Jul. 11, 2002 (111 pages).
English abstract for DE 19857887 A1 (1 page).
English abstract for DE 10335948 B3 (1 page).
Klein, Allan L. et al., "Age-related Prevalence of Valvular Regurgitation in Normal Subjects: A Comprehensive Color Flow Examination of 118 Volunteers," *J. Am. Soc. Echocardiography*, vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," *Thorac. Cardiov. Surg.*, vol. 56, pp. 328-336 (2008) (9 pages).
Gummert, J.F. et al., "Cardiac Surgery in Germany During 2006: A Report on Behalf of the German Society for Thoracic and Cardiovascular Surgery," *Thorac. Cardiov. Surg.*, vol. 55, pp. 343-350 (2007) (8 pages).

* cited by examiner

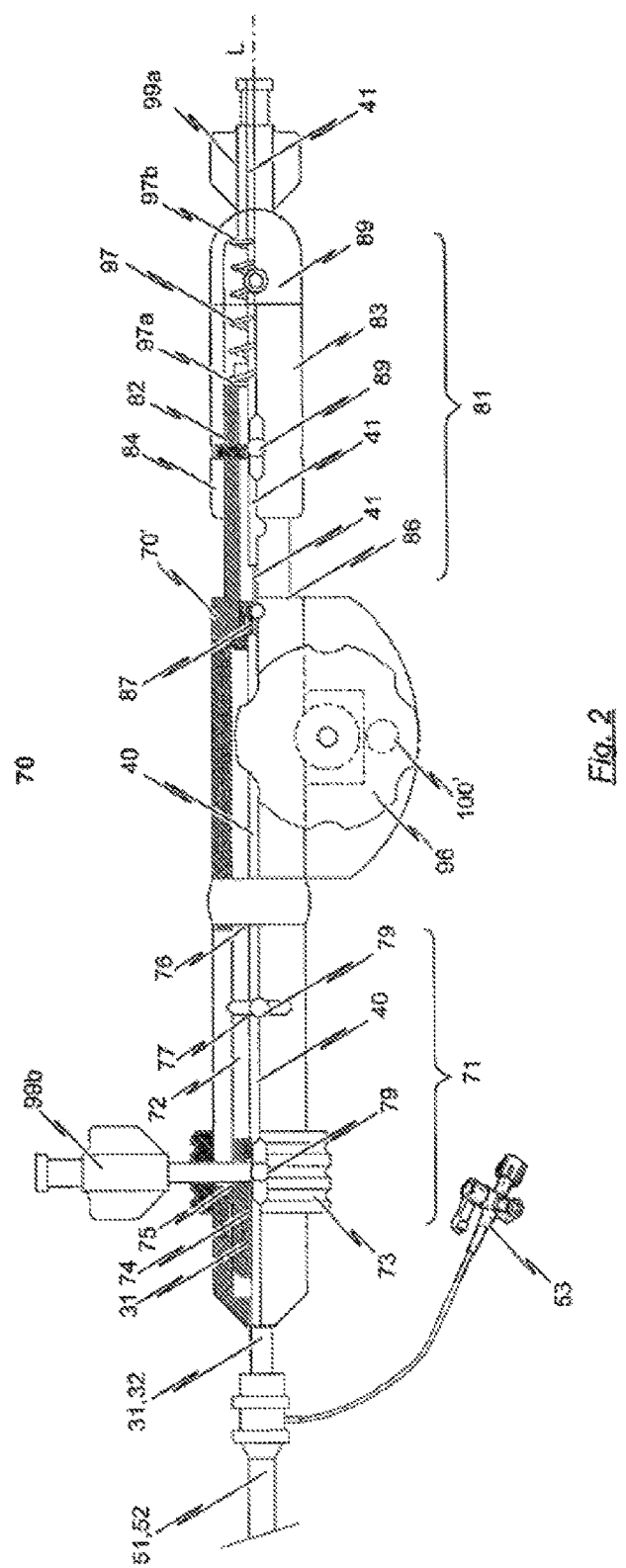

CATHETER SYSTEM FOR INTRODUCING AN EXPANDABLE STENT INTO THE BODY OF A PATIENT

CROSS-REFERENCE TO RELATED APPLICATIONS

This application is a continuation of U.S. application Ser. No. 13/698,910, filed on Mar. 18, 2013, which is the U.S. national phase entry under 35 U.S.C. § 371 of International Application No. PCT/EP2011/002524, filed on May 20, 2011, which is a continuation-in-part of, and claims priority to, U.S. application Ser. No. 12/801,090, filed on May 20, 2010, and claims priority to European Application No. 10163478.0 filed on May 20, 2010, all of which are incorporated by reference herein in their entireties.

The present disclosure concerns a catheter system for introducing an expandable heart valve stent into the body of a patient. The disclosure further concerns an insertion system comprising a catheter system and a handle for inserting an expandable heart valve stent into the body of a patient, as well as a medical device for treatment of a heart valve defect, in particular a heart valve failure or a heart valve stenosis in a patient, wherein the medical device has an insertion system and an expandable heart valve stent accommodated in the catheter tip of the insertion system.

In medical technology, there has been an endeavour over a long period to close a heart valve defect, such as an aortic valve insufficiency or an aortic valve stenosis, non-surgically by means of a transarterial interventional access by catheter, thus technically without an operation. Various insertion systems and stent systems have been proposed, with different advantages and disadvantages, which in part can be introduced into the body of a patient transarterially by means of a catheter insertion system, though a specific system has not prevailed up to the present.

The term used here "heart valve stenosis and/or heart valve insufficiency" shall generally be understood here as a congenital or acquired functional disorder of one or several heart valves. A valve defect of this type can affect each of the four heart valves, whereby the valves in the left ventricle (aortic and mitral valve) are certainly more frequently affected than those of the right heart (pulmonary and tricuspid valve). The functional disorder can result in narrowing (stenosis) or inability to close (insufficiency) or a combination of the two (combined cardiac defect).

With all known interventional systems for implantation of heart valve prosthesis, an expandable stent system is moved transarterially to an insufficient heart valve. A stent system of this type consists, for example, of a self-expanding or balloon-expanding anchoring support (also termed "heart valve stent" or "stent" in the following), to which the actual heart valve prosthesis is fastened, preferably at the distal retaining region of the anchoring support.

In the medical devices previously known from the state-of-the-art, however, it has become apparent that the implantation procedure of a stent system to which the heart valve prosthesis is attached is relatively complicated, difficult and expensive. Apart from the complicated implantation of the heart valve prosthesis as a replacement for an insufficient native heart valve, there is the fundamental risk of incorrect positioning of the stent or heart valve prosthesis with the medical devices used up to the present, which cannot be corrected without more extensive operative intervention.

The problem addressed by the present disclosure is the fact that medical technology does not currently offer any insertion system in particular for transarterial or transfemoral implantation of a self- or balloon-expandable heart valve stent with a heart valve prosthesis attached to it in which, on the one hand, the insertion system enables a minimally invasive implantation of the heart valve prosthesis in a predictable manner and, on the other, dispensing with the need to use a heart-lung machine during the operation on the anaesthetized patient. Consequently the operative intervention can be designed to be especially cost-effective and, in particular, to reduce the physical and mental stress on the patient. In particular, there is a lack of a medical device for implantation of heart valve prostheses that can also be used for patients on whom, due to their age, an operation cannot be carried out without the aid of a heart-lung machine.

Because of the increasing number of patients requiring treatment, there is also a growing need for an insertion system with which a minimally invasive intervention can be made on a patient for treatment of a heart valve stenosis and/or heart valve insufficiency in a precisely predictable way, whereby the success of the operation is in particular no longer significantly dependent on the skill and experience of the heart surgeon or radiologist carrying out the treatment.

This situation also applies to operations in which heart valve prostheses with stent systems are implanted with the aid of a so-called balloon catheter system.

It is also regarded as problematic that, when using systems already known from the state-of-the-art by means of which a heart valve prosthesis can be implanted in the body of the patient with minimal invasiveness, incorrect positioning of the heart valve prosthesis or the associated heart valve stent can frequently only be avoided when the heart surgeon or radiologist is especially experienced. It is indeed known, for example, to insert a heart valve stent with a heart valve prosthesis attached to it into the body of a patient as far as the heart via the aorta, whereby self-expansion or balloon-expansion of the heart valve stent is initiated by external manipulation when the implantation location is reached, which should lead to a secure anchorage and precise positioning of the heart valve prosthesis; such heart valve stents cannot usually be removed in a simple way, however, and their position cannot usually be corrected once the stent has expanded.

Accordingly, there is basically a risk with the known systems that if, for example, the self-expansion or balloon-expansion of the heart valve stent with the attached heart valve prosthesis is initiated in a non-optimum position, due to a slip by the doctor carrying out the treatment or other technical circumstances such as stent foreshortening, this position can only be corrected appropriately by means of a major, in particular operative, intervention, which must frequently be carried out on the open heart.

For example, a heart valve stent for heart valve prosthesis is described in document WO 2004/019825 A1. With this heart valve stent, distal-end support arches or hoops and positioning arches or hoops are provided, which can be inserted into the pockets of the native heart valve of a patient so that the heart valve stent can be positioned by means of the support hoops. Additional so-called commissural hoops can also be formed on the known heart valve stent which, together with the support arches, clamp parts of the old heart valve once the stent has unfolded to that the stent can be positioned and anchored as a result of this clamping action.

Although the support arches provided on the anchoring stent enable improved positioning of the heart valve prosthesis to be implanted, there is nevertheless still a risk of incorrect implantation and of the heart valve prosthesis being incapable of functioning correctly or functioning but unsatisfactorily. For example, it may be found during the intervention that the heart valve prosthesis or the heart valve stent is not optimally dimensioned for the patient. In such cases, even if only the respective distal support or positioning arches of the stent are in their expanded state, removal (explantation) or repositioning of the heart valve stent with the heart valve prosthesis is no longer possible and there exists an increased mortality risk for the particular patient.

The aortic arch in the human body represents a further problem for such interventions, since it has to be accessed during insertion through the aorta. When this is done, the catheter tip and the respective catheter must undergo a change of direction of approximately 180° over a relatively small radius, usually about 50 mm, without causing injury or damage to the vessel wall.

The objective of the disclosure is to propose a catheter system for introducing an expandable heart valve stent into the body of a patient and for positioning the stent at a desired implantation site, wherein the catheter system is designed to enable the implantation of a heart valve prosthesis attached to a heart valve stent in the optimum implantation location in a sequence of events defined before the intervention.

Secondly, the objective is to propose a medical device for treatment of a heart valve stenosis and/or heart valve insufficiency, comprising a catheter system and an expandable heart valve stent mounted in the catheter tip of the insertion system and which is designed to reduce the risk to the patient on implantation of the heart valve prosthesis.

In accordance with a preferred embodiment, the present disclosure provides a catheter system for introducing an expandable heart valve stent into the body of a patient, the catheter system comprising a catheter tip and a catheter shaft. The catheter tip of the catheter system has a seat portion for accommodating the stent to be introduced into the patient's body in its collapsed state. The catheter system has further a stent holder for realisably fixing the stent to the catheter tip. The seat portion of the catheter tip is constituted by a first sleeve-shaped member and a second sleeve-shaped member, said sleeve-shaped members being moveable relative to each other as well as relative to the stent holder of the catheter tip. The catheter shaft comprises first force transmitting means, second force transmitting means and guiding means. The distal end section of the first force transmitting means is connected to the first sleeve-shaped member of the catheter tip and the proximal end section of the first force transmitting means is connectable to a first operating means of a handle. The distal end section of the second force transmitting means is connected to the second sleeve-shaped member of the catheter tip and the proximal end section of the second force transmitting means is connectable to a second operating means of the handle.

Preferably, the cross-section of second sleeve-shaped member of the catheter tip is equal to or less than the cross-section of the first sleeve-shaped member of the catheter tip. In case the cross-section of second sleeve-shaped member of the catheter tip is less than the cross-section of the first sleeve-shaped member, the second sleeve-shaped member is at least partly accommodatable within the first sleeve-shaped member in a telescopic manner. This may allow minimizing the cross-section of catheter tip. At the same time, an expandable heart valve stent may be released from the catheter tip of the catheter system in a step-wise manner. In case the cross-section of second sleeve-shaped member of the catheter tip is less than the cross-section of the first sleeve-shaped member, the second sleeve-shaped member and the first sleeve-shaped member—once brought together—can reside on an internal support structure, e.g. a cylindrical insert, resulting in a step and gap free transition.

According to one aspect of the present disclosure, the catheter system comprises guiding means having a guiding tube with a passageway extending there between. The guiding means serves for guiding of the catheter shaft has a distal end, a proximal end and a passageway extending there between. The first and second force transmitting means are at least partly received within this passageway such as to be moveable relative to the guiding means. The guiding tube of the guiding means has a length such that the distal end of the guiding means terminates proximal to the catheter tip of the catheter system. Moreover, guiding tube has a cross-section less than the cross-section of the catheter tip.

According to another aspect of the present disclosure, the catheter system further comprises a guide wire suited for guiding the catheter tip of the catheter system to an implantation site. The guide wire is designed to be advanced into a patient's vasculature independently from the catheter system and, in particular, independently from the catheter tip of the catheter system.

In accordance with another preferred embodiment, an insertion system for inserting an expandable heart valve stent is disclosed.

Whilst the term "vascular" refers to the blood vessels of the patient's body including both veins and arteries, in a preferred embodiment, the insertion system is for transarterial delivery using the arteries, although it is conceivable that in other embodiments transvenous delivery via a vein could be used.

In particular, the vascular insertion system comprises a catheter system with a catheter tip, a catheter shaft and a handle. The catheter tip has a seat portion for accommodating a stent to be inserted in its collapsed state and a stent holder for releasably fixing the stent. The proximal end of the catheter system is attached to the handle and the distal end is attached to the catheter tip. The catheter system comprises the catheter shaft for connecting the catheter tip to the handle of the insertion system, the distal end section of the catheter shaft being flexible enough such that the catheter tip and the distal end section of the catheter shaft may be easily navigated through the anatomy and especially through the aortic arch during insertion through the aorta of the patient.

The handle has at least one first and one second operating means with which the catheter tip of the insertion system may be appropriately manipulated so that an expandable stent housed in the catheter tip may be released from the catheter tip in steps or in a defined or definable sequence of events.

The catheter tip of the catheter system and at least the distal part of the catheter shaft are typically inserted into the femoral artery and moved up the descending thoracic aorta until the catheter tip is positioned in the ascending aorta. The proximal end of the catheter shaft together with the handle attached thereto remains outside of the patient's body.

In accordance with a preferred embodiment, the catheter tip has first and second housing portions termed "sleeve-shaped members" in the following, that may be manipulated with the handle. These sleeve-shaped members are used for accommodating specific portions of the stent. The first sleeve-shaped member is used for accommodating first functional components of the stent, for example retaining hoops of the stent (or alternatively positioning hoops of the stent), while the second sleeve-shaped member is used for accommodating the second functional components of the stent, for example, positioning hoops of the stent (or alternatively for accommodating retaining hoops of the stent).

In relation to the handle provided for the insertion system, it is preferably provided that, on one hand, the first operating means cooperate with the first sleeve-shaped member of the catheter tip so that, on actuation of the first operating means, a previously definable longitudinal displacement of the first sleeve-shaped member may be effected relative to the stent holder and the guiding tube of the catheter shaft. On the other hand, the second operating means cooperates with the second sleeve-shaped member of the catheter tip so that a previously definable longitudinal displacement of the second sleeve-shaped member may be affected relative to the stent holder and the guiding tube of the catheter shaft.

The cross-section of the second sleeve-shaped member is identical to the cross-section of the first sleeve-shaped member such that the sleeve-shaped members can completely enclose a stent accommodated in the catheter tip without a gap between the first and second sleeve-shaped members thereby providing a catheter tip having an atraumatic shape. In addition, the first and second sleeve-shaped members are movable relative to each other and relative to the stent holder.

For this purpose, first force transmitting means with a distal end section connected to the first sleeve-shaped member and a proximal end section connected to first operating means of the handle are provided. In addition, second force transmitting means with a distal end section connected to the second sleeve-shaped member and a proximal end section connected to second operating means of the handle are provided. When manipulating the first and/or second operating means of the handle, the first and/or second sleeve-shaped members may be moved relative to each other and relative to the stent holder.

In accordance with the preferred embodiment, the first force transmitting means is constituted by a first catheter tube defining a first lumen and the second force transmitting means is constituted by a second catheter tube defining a second lumen. The second catheter tube has a cross-section less than the cross-section of the first catheter tube. The first catheter tube is disposed concentrically and coaxially with the second catheter tube and the second catheter tube is received within the first lumen defined by the first catheter tube.

Contrary to the first and second sleeve-shaped members of the catheter tip, however, the stent holder of the catheter tip is not moveable relative to the handle of the insertion system. Rather, the stent holder is connected to the handle by using a stent holder tube having a distal end connected to the stent holder and a proximal end connected to a body of the handle. The stent holder tube has a cross-section less than the cross-section of the first catheter tube. In particular, the first catheter tube is disposed concentrically and coaxially with both, the second catheter tube on the one hand and the stent holder tube on the other hand. Preferably, the stent holder tube has a cross-section less than the cross-section of the first catheter tube and greater than the cross-section of the second catheter tube such that the stent holder tube is received within the first lumen defined by the first catheter tube and the second catheter tube is received within a passageway defined by the stent holder tube. The passageway defined by the stent holder tube has a diameter sufficient to accommodate the second catheter tube such that the second catheter tube is moveable relative to the stent holder tube.

The second lumen defined by the second catheter tube has a diameter sufficient to accommodate a guide wire. The second catheter tube is made from a rigid material including, for example, nitinol, stainless steel or a rigid plastic material.

The material of the distal end section of the second catheter tube may have an increased flexibility compared to the material of the proximal end section in order to allow the distal end section of the catheter shaft to pass the aortic arch during insertion of the catheter tip.

The distal end section of the second catheter tube terminates in a soft catheter end tip having an atraumatic shape. The soft catheter end tip is provided with a channel aligned with the second lumen defined by the second catheter tube such that a guide wire accommodated within the second lumen of the second catheter tube may pass through the channel of the soft catheter end tip. The second sleeve-shaped member of the catheter tip is connected to the soft catheter end tip such that the opened end of the second sleeve-shaped member faces in the proximal direction opposite to the direction of the soft catheter end tip and to the second catheter tube.

The stent holder tube is made of a rigid material, for example, a rigid plastic material, stainless steel or nitinol. The distal end of the stent holder tube terminates in the stent holder which is also made of a rigid material, for example, a rigid plastic material or stainless steel. The passageway defined by the stent holder tube is aligned with a channel which passes through the stent holder. In this way, the second catheter tube is accommodated in the passageway of the stent holder tube and the channel of the stent holder such as to be moveable relative to the stent holder tube and the stent holder. The stent holder tube is provided for connecting the stent holder to the handle. For this purpose, the stent holder tube has a distal end connected to the stent holder and a proximal end connected to a body of the handle.

The first catheter tube is made of a bendable but inelastic material. For example, the first catheter tube may be at least partly made of a braided or non-braided catheter tube. Hence, the first catheter tube has a stiff braid reinforced body similar to the catheter body described in U.S. Pat. No. 4,665,604 which is incorporated herein by reference.

The first catheter tube shall be adapted to transfer compression and tension forces from the first operating means of the handle to the first sleeve-shaped member of the catheter tip without overly changing of its total length. The distal end of the first catheter tube terminates at a flared section as the transition to the section defining the first sleeve-shaped member of the catheter tip. The flared section and the first sleeve-shaped member may be formed integrally and may be connected to the distal end section of the first catheter tube. Alternatively, the first sleeve-shaped member and the flared section of the first catheter tube may be all of the same material and originating from the same raw tube prior to a widening process so that the flared section and the first sleeve-shaped member are the same elements.

The insertion system according to the preferred embodiment further comprises a guiding tube having a cross-section greater than the cross-section of the first catheter tube. The guiding tube defines a passageway and is disposed concentrically and coaxially with the first catheter tube, the stent holder tube and the second catheter tube such that the first catheter tube with the stent holder tube and the second catheter tube accommodated therein is at least partly accommodated within the passageway defined by the guiding tube, wherein the first catheter tube is moveable relative to the guiding tube. In particular, the guiding tube terminates proximal to the catheter tip wherein the cross-section of proximal end section of the guiding tube shall be substantially the same as or less than the cross-section of the flared section provided at the proximal end of the first catheter tube. The proximal end section of the guiding tube terminates distal to the handle. The proximal end section of the guiding tube may be detached/disconnected from the handle so that the handle as well as the first and second catheter tubes and the stent holder tube together with catheter tip may be moved relative to the guiding tube.

The distal end of the guiding tube is formed such that the flared section provided at the distal end section of the first catheter tube may abut on the distal end of the guiding tube without abrupt transition. The guiding tube may be of a thin material such as to allow length deformation of the guiding tube upon transfer of compression and tension forces. The guiding tube material, however, shall have sufficient stiffness in order to mechanically avoid kinking of the flexible sections of the distal portion of the catheter shaft during insertion of the catheter tip.

The proximal end of the guiding tube is releasably connectable to the body of the handle. In this way, the guiding tube may have a double-function:

In case, the proximal end of the guiding tube is connected to the handle, the guiding tube serves as a distal extension of the body of the handle relative to which the first and second operating means are moveable for manipulating the first and second sleeve-shaped members of the catheter tip. Hence, position of the stent holder relative to the native heart valve of the patient may be changed by moving the guiding tube connected to the handle.

In case, the proximal end of the guiding tube is not connected to the body of the handle, the guiding tube may serve as a portal for passing the catheter shaft of the catheter system into the patient's body from proximal of the catheter tip.

In any case, the guiding tube has a length and is adapted such that the first catheter tube and the second catheter tube are moveable relative to each other and relative to the stent holder independent from any movement or activation of the guiding tube. In particular, the movement of the sleeve shaped members is independent from the presence or absence of the guiding tube. The length of the guiding tube is such that the sleeved shaped members and hence the first and second catheter tubes are moveable relative to each other and relative to the stent holder without interfering with the distal end of the guiding tube.

An inlet may be provided at a proximal end section of the guiding tube for injection of fluids into the guiding tube. Furthermore, a check valve may be provided at the proximal end section of the guiding tube to prevent fluid from leaking out of the guiding tube.

The guiding tube may have a length sufficient to protect the inner wall of the blood vessel through which the catheter tip passes. In addition, a separate introducer system (not belonging to the catheter system) may be provided. The introducer system then may serve as a portal for passing the complete catheter system from the catheter tip to the catheter shaft into the patient's body and up to the heart.

In addition, the guiding tube reduces the compression force exerted on the first catheter tube that is inserted through the guiding tube. This increases manoeuvrability of the first catheter tube throughout the procedure in which the first catheter tube serves as force transmitting means for manipulating the first sleeve-shaped member of the catheter tip. A consequence thereof is that the frictional force acting on the first catheter tube is reduced compared with a catheter design which is not provided with a guiding tube. Moreover, moving the catheter tip after it has been advanced through the vascular system of a patient, is greatly improved while at the same time lowering the risk of injury of the patient.

In accordance with the preferred embodiment, the guiding tube has a cross-section equal to or less than the cross-section of the catheter tip. In this regard, the guiding tube will have a length shorter than the length of the first and second catheter tubes such that the distal end of the guiding tube terminates proximal to the catheter tip. As will be appreciated, the guiding tube may not be removed from the catheter system in case the proximal end sections of the first and second catheter tube are connected to the respective operating means of a handle.

The length of the guiding tube depends on the length of the first and second catheter tubes and will typically be between about 20 cm and 100 cm. Those skilled in the art will appreciate, however, that all dimensions provided herein are intended as examples only, and that the guiding tubes and catheter tubes of different dimensions may be substituted for a particular use. As already indicated, the first and second catheter tubes are moveable relative to each other and relative to the stent holder independent from the guiding tube. The movement of the sleeve shaped members is independent from the presence or absence of the guiding tube. In other words, the guiding tube does not serve for manipulating the sleeve-shaped members of the catheter tip. In particular, the guiding tube does not block the travel of the sleeve-shaped members.

As will be appreciated, the guiding tube will be of a size, i.e. has an outer diameter, which will permit insertion in a patient's blood vessel (artery or vein) which is used for moving the stent transarterially or via a vein to an insufficient heart valve.

The guiding tube may be capable of traversing tortuous pathways in the body of the patient without kinking. The guiding tube may include an inner lubricious liner, an outer polymeric jacket, and a coil reinforcement between the inner and the outer layers. This guiding tube may provide favourable flexibility without kinking or compression. One or more radiopaque bands or markers may be incorporated within the guiding tubes material to allow precise location of the guiding tubes distal end for positioning accuracy. Those skilled in the art will appreciate that other known materials may also be suitable for a particular purpose.

In an embodiment disclosed herein, the catheter tip and the catheter shaft proximally connected to the catheter tip may be inserted into the patient's body by using a guide wire. The guide wire serves for guiding the catheter tip of the catheter system to an implantation site. Once in position above the aortic valve the guide wire may then be removed. Alternatively, the guide wire remains in the patient's body during implantation of a heart valve prosthesis accommodated in the catheter tip. Then, the guide wire is removed together with the catheter from the patient's body.

The guide wire is designed to be advanced into a patient's vasculature independently from the catheter tip and the catheter shaft proximally connected to the catheter tip. In other words, the catheter tip together with at least the distal part of the catheter shaft and the guide wire are advanced as single units through the vasculature of the patient, respectively. Once the guide wire is placed, the catheter tip and the catheter shaft proximally connected to the catheter tip can be advanced over the guide wire directly to the particular site in the patient's cardiovascular system.

In accordance with the present invention, a guide wire is advanced through the patient's vascular system, its direction being controlled and fluoroscopically monitored by the surgeon, until its distal end is at the desired location. Preferably, the guide wire is very small in diameter, thereby not presenting any substantial obstruction to blood flow in the blood vessel. After inserting the guide wire, the catheter tip together with the catheter shaft proximally connected to the catheter tip are advanced over the guide wire with the wire being received in the second lumen which is defined by the second catheter tube of the catheter shaft. The guide wire thus simply and automatically guides the catheter tip of the catheter system directly to the intended region, without requiring difficult, time consuming manipulations.

In a preferred embodiment of the present disclosure, the guide wire has a diameter less than the diameter of the second lumen defined by the second catheter tube. This allows that the guide wire may be at least partly received within the second lumen defined by the second catheter tube for guiding the catheter tip, at least partly disposed about the guide wire, to the implantation site.

In a preferred embodiment of the invention, the second lumen defined by the second catheter tube of the catheter shaft has a minimum dimension which is just slightly greater than the diameter of the guide wire. The maximum cross-sectional dimension of the second lumen is substantially larger than the cross-section of the guide wire. Thus, when the guide wire is disposed within the second lumen there will be substantial voids through the second lumen, on opposite sides of the guide wire through which fluids may be administered to the patient and through which blood pressure measurements may be taken. Such fluids may be administered and pressure measurements may be taken without removing the guide wire at all. By way of example, the cross-section of the guide wire preferably is of the order of no more than about fifty percent of the cross-sectional area of the second lumen.

In order to implant a heart valve prosthesis accommodated in the catheter tip, the catheter tip and the catheter shaft proximally connected to the catheter tip are advanced over the guide wire. As the tip of the guide wire terminates in the left ventricle of the heart, pushing the guide wire may contact the left ventricular apex.

In order to avoid any damage of the left ventricular apex when the guide wire is inserted, and to avoid any injury or damage to the vessel wall when the guide wire is inserted (advanced) through a vessel, the guide wire preferably has a flexible bumper at the leading end of the advancing guide wire, which minimizes the risk of trauma or injury to the delicate internal surfaces of the artery. The bumper is preferably highly flexible and with a smooth leading end. For example, the guide wire may terminate in a smoothly surfaced rounded tip, at the distal end of the guide wire. Alternatively, the distal end of the guide wire may have a j-hook shape or a hockey-stick shape, thereby reducing the risk of trauma.

Since the guide wire and the catheter tip together with the catheter shaft proximally connected to the catheter tip are generally independently advanced into the vasculature, the guide wire must be sufficiently stiff throughout its length to prevent buckling. Furthermore, the guide wire shall have sufficient stiffness to track the delivery system (catheter tip and catheter shaft proximally connected to the catheter tip) around the aortic arch. On the other hand, at least the distal tip of the guide wire shall be soft enough to prevent puncture of the heart tissue.

The guide wire may comprise a distal tip guide section and a proximal pull section. The pull section allowing for the tip guide section to be pulled out after final positioning of the catheter tip and having an optimal cross sectional area and size, is generally smaller than that of the tip guide section so as to assure minimum blood leakage at the insertion site. The tip guide section is capable of guiding the catheter through a patient's vasculature.

The guide wire may, in an exemplary embodiment, be approximately 175 centimeters long so that it may be introduced through the femoral artery and have ample length to reach the patient's coronary region. The guide wire may include a small diameter main wire. This rotationally rigid main wire of the guide wire can be solid or tubular, as long as it is rigid torsionally so that it may transmit fully to the distal end a rotational motion imparted to the proximal end. The main wire has relatively little twist as its proximal end is rotated. Practically all rotation applied to the proximal end will be transmitted quickly to the very distal tip of the guide wire. Alternatively, the guide wire may be formed substantially from elongate helical springs.

As already indicated, the aortic arch in the human body may represent a challenge for transfemoral implantation of a self- or balloon-expandable heart valve stent with a heart valve prosthesis attached to it, since it has to be accessed during insertion through the aorta. When this is done, the catheter tip and the catheter shaft proximally connected to the catheter tip must undergo a change of direction of approximately 180° over a relatively small radius, usually about 50 mm, without causing injury or damage to the vessel wall. For aiding the bending of the catheter tip and the catheter shaft proximally connected to the catheter tip when passing through the aortic arch and for supporting the catheter tip in accessing the ascending aorta, the guide wire may have a specific structure such as to make a U turn in the aortic arch. Hence, the guide wire may be programmed such that the guide wire takes a U-shape bend.

In a preferred embodiment of the present disclosure, at least a distal section of the guide wire has a predefined curved configuration adapted to the curvature of the patient's aortic arch. The predefined curved configuration of at least the distal section of the guide wire is selected such as to push the catheter tip in the direction of the centre of the ascending aorta when the catheter tip is at least partly disposed about the distal section of the guide wire and transfemoral inserted into the patient's body.

In this respect, the guide wire has a double-function: On the one hand, the guide wire serves for guiding the catheter tip of the catheter system to an implantation site. On the other hand, the guide wire serves for positioning the catheter tip in the centre of the ascending aorta when the catheter tip has accessed the ascending aorta. Then, positioning arches or hoops of the stent accommodated in the catheter tip may be easily inserted into the pockets of the native heart valve of a patient so that the heart valve stent can be easily positioned.

In a preferred embodiment, at least the distal section of the guide wire exhibits a first predefinable shape before advancing the guide wire into the patient's vasculature and a second predefinable shape in the advanced state of said guide wire, wherein the second predefinable shape of the distal section of the guide wire corresponds to the predefined curved configuration of the distal section of the guide wire. For achieving this, the guide wire may consist at least partly of a shape memory material such that at least the distal section of the guide wire can transform from a temporary shape into a permanent shape under influence of an external stimulus, wherein the temporary shape of the distal section of the guide wire corresponds to the first shape and the permanent shape of the distal section of the guide wire corresponds to the second shape.

A shape memory material, for example Nitinol, may be used as the material for at least the distal section of the guide wire. Such a shape memory material is preferably designed such that the guide wire can transform from a temporary shape into a permanent shape under the influence of an external stimulus. The temporary shape is thereby the first shape of the guide wire (i.e. the shape of the guide wire before inserting it into the patient's body), while the permanent shape is assumed in the second shape of the guide wire (i.e. in the inserted state of the guide wire). In particular, use of a shape memory material such as Nitinol, i.e. an equiatomic alloy of nickel and titanium, allows for a particularly gentle insertion procedure.

It is conceivable of course that other shape memory materials, for example shape-memory polymers, are used as the material for at least the distal section of the guide wire. At least parts of the guide wire may be formed by using, for example, a polymer composite exhibiting a crystalline or semi-crystalline polymer network having crystalline switching segments. On the other hand, an amorphous polymer network having amorphous switching segments is also conceivable.

When manufacturing the guide wire preferably made from a shape memory material, the permanent shape of the guide wire, i.e. the shape of the guide wire which is assumed in the inserted state of the guide wire, is formed. Once the desired shape has been formed, this shape is "fixed", this process being known as "programming". Programming may be effected by heating the guide wire, forming the guide wire into the desired shape and then cooling the guide wire. Programming may also be effected by forming and shaping the structure of the guide wire at lower temperature, this being known as "cold stretching." The permanent shape is thus saved, enabling the guide wire to be stored and implanted in a temporary, non-formed shape. If an external stimulus then acts on the stent structure, the shape memory effect is activated and the saved, permanent shape restored.

A particularly preferred embodiment provides for the external stimulus to be a definable switching temperature. It is thus conceivable that the material of the guide wire needs to be heated to a higher temperature than the switching temperature in order to activate the shape memory effect and thus regenerate the saved permanent shape of the guide wire. A specific switching temperature can be preset by the relevant selection of the chemical composition of the shape memory material.

It is particularly preferred to set the switching temperature to be in the range of between 10° C. and the patient's body temperature and preferably in the range of between 10° C. and room temperature (22° C.). Doing so is of advantage, especially with regard to the guide wire which needs to be inserted in a patient's body. Accordingly, all that needs to be ensured in this regard when inserting the guide wire is that the guide wire is warmed up to room temperature or the patient's body temperature (37° C.) at the site of implantation to activate the shape memory effect of the stent Material.

Alternatively, the guide wire may be made from another material (for example a platinum-tungsten alloy) which allows that the distal region of the guide wire can be bent manually by the surgeon and will retain its bent configuration when relaxed. This enables the guide wire to be controllably steered by rotation of the guide wire to direct the curved distal end selectively into the aortic arch and into the ascending aorta. Rotational control of the guide wire may be enhanced by bending the proximal end of the wire to form somewhat of a handle.

In use, the surgeon may bend the distal region of the guide wire so that it will be biased toward and will assume somewhat of a curve when relaxed. When advanced through the patient's artery the degree of resilience at the distal region of the wire is such that the wire will straighten and follow the path of the artery quite easily. A progressively increased flexibility resulting from, for example, a continuous taper at the distal region of the guide wire may enhance the ability of the guide wire to flex from the pre-bent biased curve and follow the path of the blood vessel.

When the distal end of the pre-bent, biased guide wire is at the descending aorta proximal of the aortic arch, the surgeon can steer it into the aortic arch and thereafter into the ascending arch by rotation of the guide wire by manipulating it from the proximal end.

Alternatively, the guide wire may be inserted into the patient's body by using a guide catheter. The guide catheter may comprise a guide catheter tube defining a lumen for receiving the guide wire. The guide catheter may serve for inserting the guide wire. Once the guide catheter is introduced through the femoral artery and the aortic arch and has reached the patient's aortic valve region, the guide wire is released from the guide catheter by removing the guide catheter whereas the guide wire remains in the patient's body. In this case, the guide wire exhibits its first predefinable shape before releasing the guide wire from the guide catheter and its second predefinable shape after releasing the guide wire from the guide catheter. As already indicated, the second predefinable shape of the distal section of the guide wire is selected such that the distal section of the guide wire pushes the catheter tip in the direction of the centre of the ascending aorta when the catheter tip is at least partly disposed about the distal section of the guide wire and transfemoral inserted into the patient's body.

According to one aspect of the present disclosure, at least the distal region of the guide wire is at least partly formed from a material having a high radiopacity. A relatively high degree of radiopacity of the distal region of the guide wire enhances fluoroscopic imaging of the guide wire as it is advanced through the patient's artery.

The procedure for using the guide wire in accordance with the present invention involves initial placement and location of the guide wire in the femoral artery and the aortic arch. Once the guide wire is in place the catheter tip with the catheter shaft of the catheter system then may be advanced over the guide wire to a point where the stent accommodated in the catheter tip is in the ascending aorta proximal to the native aortic heart valve. This can be verified fluoroscopically because of the highly radiopaque characteristic of the catheter tip and/or guide wire and also by injecting radiopaque dye through, for example, a lumen of the catheter system. For this reason, the catheter tip of the catheter system may be provided with radiopaque markers which also facilitate fluoroscopic monitoring of its progress and position.

In order to treat a heart valve stenosis and/or heart valve insufficiency in a patient, a medical device is disclosed. The medical device comprises an insertion system and an expandable heart valve stent accommodated in the catheter tip of the insertion system. While it is accommodated in the catheter tip of the insertion system, the stent adopts a first previously definable configuration. Outside the catheter tip or in the implanted state, however, the stent exists in a second previously definable configuration. The first configuration of the stent corresponds to the folded-up state, while the stent exists in its expanded state in the second configuration.

A heart valve stent is used with the medical device, as described for example in the European Patent Application No. 07 110 318 or in the European Patent Application No. 08 151 963. In a preferred embodiment of the medical device, a heart valve stent is accordingly used which exhibits the following:

- a first retaining region, to which a heart valve prosthesis can be attached;
- an opposing, second retaining region with at least one retaining element, for example in the form of retaining eyes or in the form of retaining heads, whereby at least one retaining element of the stent can be put in releasable engagement with the stent holder of the catheter tip forming part of the insertion system;
- at least one retaining hoop, to which a heart valve prosthesis can be fastened; and
- at least one and preferably three positioning hoops, which are designed to engage in pockets of the native heart valve in the implanted state of the stent, thus to enable automatic positioning of the stent in the aorta of the patient.

In particular, an insertion system is proposed, with which an expandable heart valve stent with a heart valve prosthesis attached to this stent can be advanced to the implantation site in a particularly simple way, for example via the aorta of a patient being treated (transarterially or transfemorally). Preferably, during transarterial or transfemoral access by the catheter system, the whole free cross-section available within the aorta is not completely filled up, since the catheter tip provided at the distal end region of the catheter system, in which the stent can be accommodated with the heart valve prosthesis, can be made sufficiently small with respect to its external diameter.

The expandable heart valve stent with the heart valve prosthesis attached to it can be accommodated temporarily during implantation in the folded-up state in the catheter tip of the insertion system, which is provided at the distal end region of the catheter system. The catheter system may be of a length sufficient to allow the catheter tip provided at the distal end region of the catheter system to be guided through the aorta to the patient's heart by insertion at the patient's groin.

The insertion system designed for transarterial or transfemoral access is therefore suitable for inserting a heart valve stent with a heart valve prosthesis attached to it, transarterially or transfemorally into the body of the patient; for example, the catheter system of the insertion system is inserted with the catheter tip located at the distal end of the catheter system via puncture of the *A. femoris communis* (inguinal artery).

In particular, with the insertion system designed for transarterial or transfemoral access, the catheter system may be designed so that it is both kink-resistant and flexible such that a bending radius of up to 4 cm, and preferably up to 3 cm, can be realised, at least at the distal end region of the catheter system.

Preferred embodiments will be described with reference to the appended drawings below.

Figure 3A:
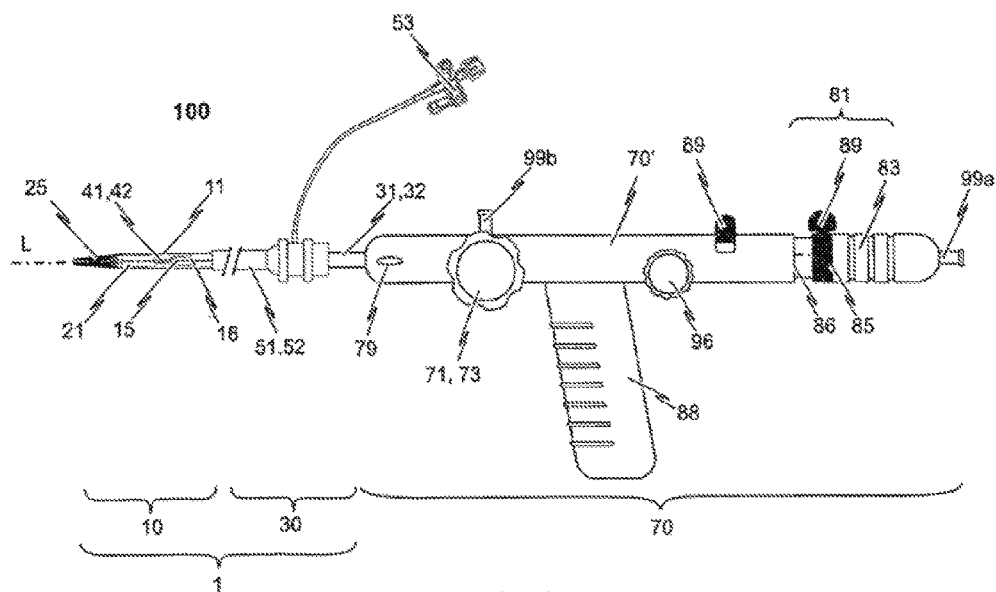
Figure 3B:
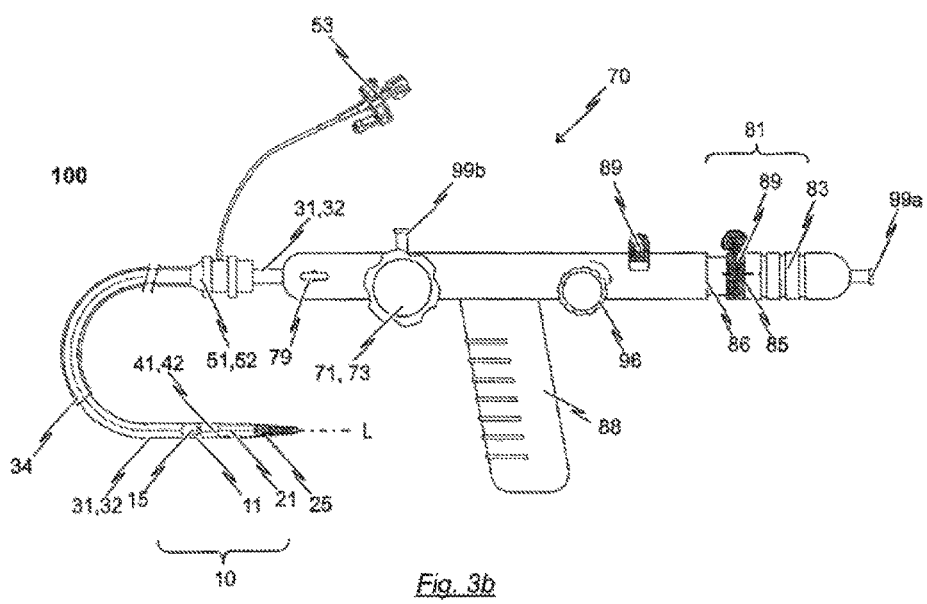
Figure 4:
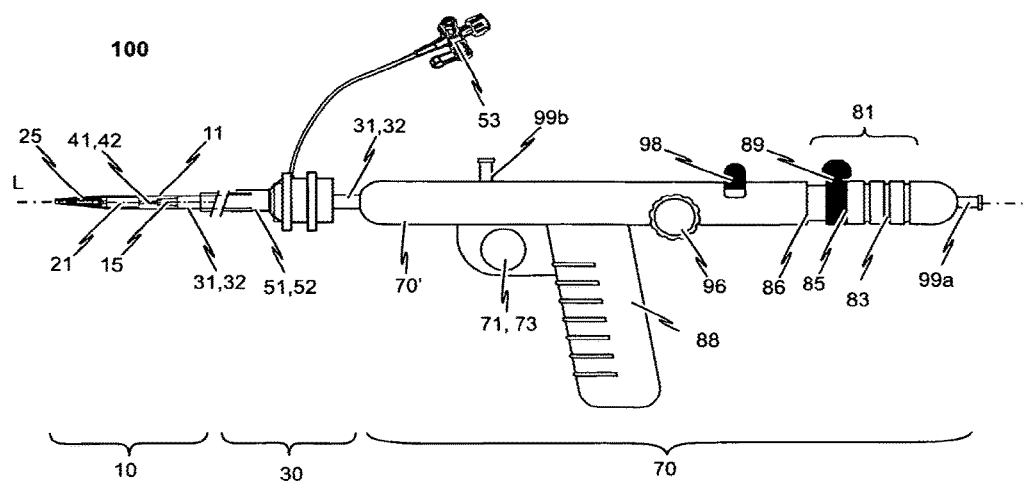
Figure 5:
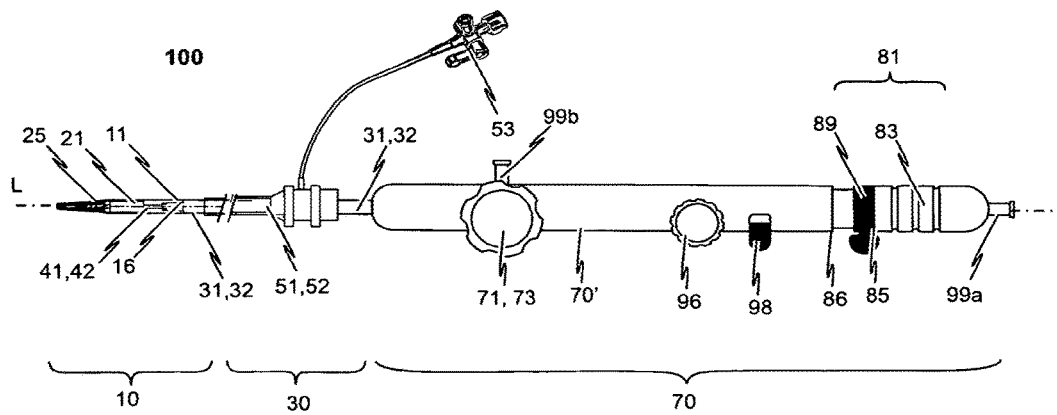
Figure 8:
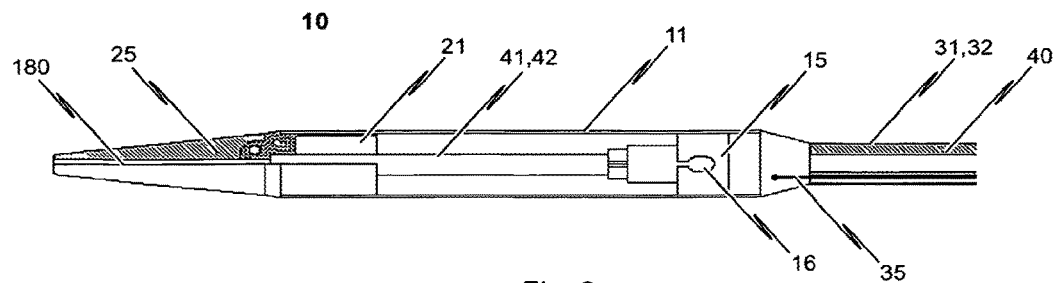
Figure 9:
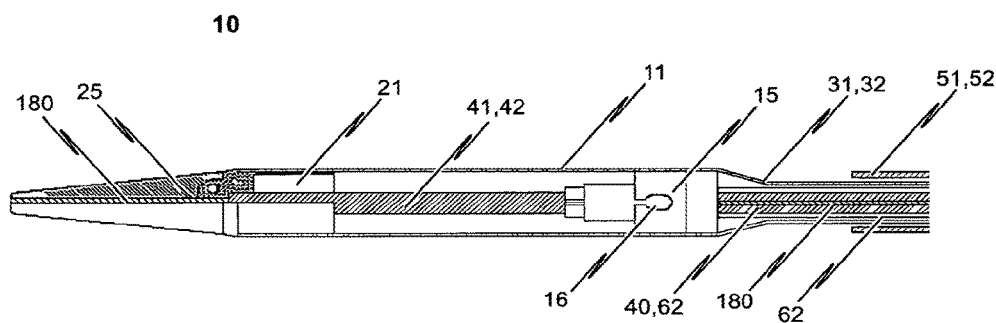
Figure 10A:
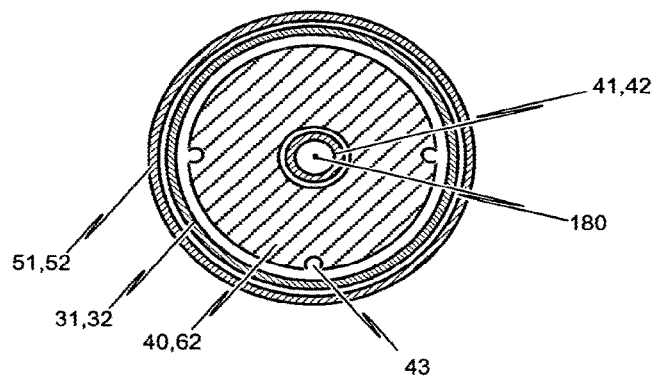
Figure 10B:
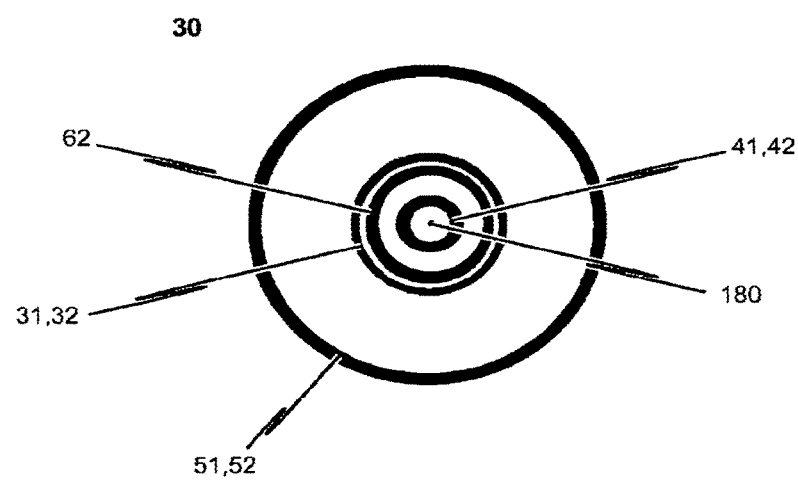
Figure 11:
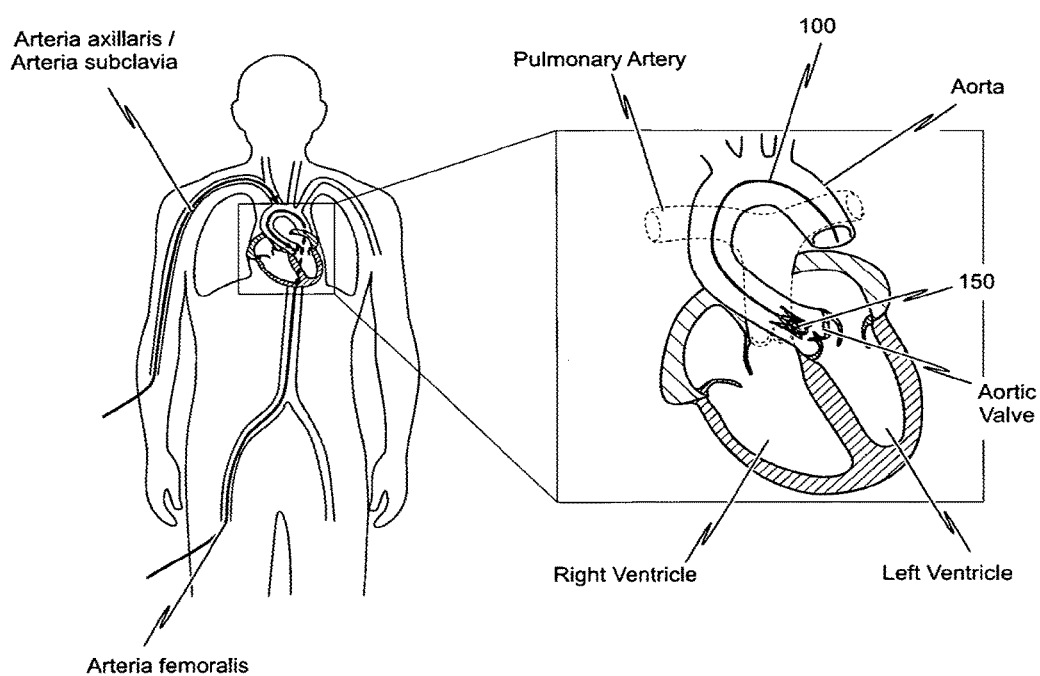
Figures 12A, 12B, 12C:
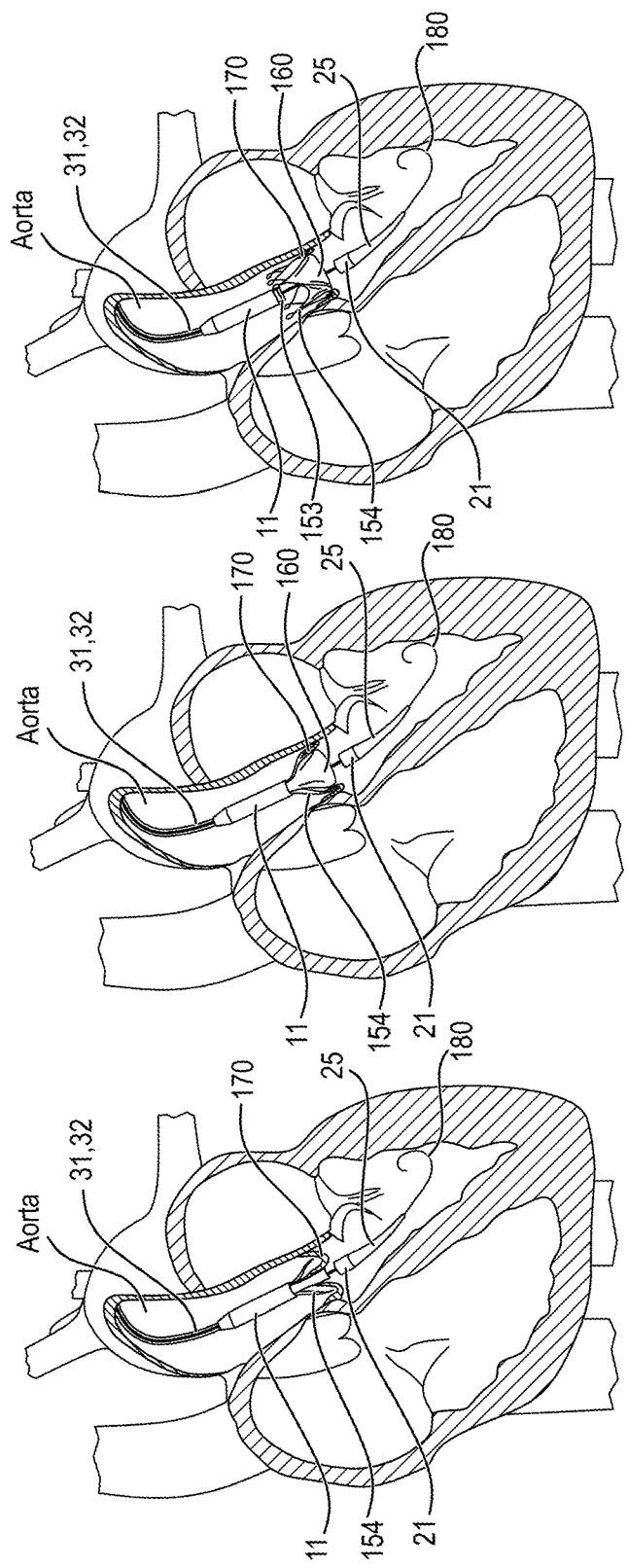
Figure 13A:
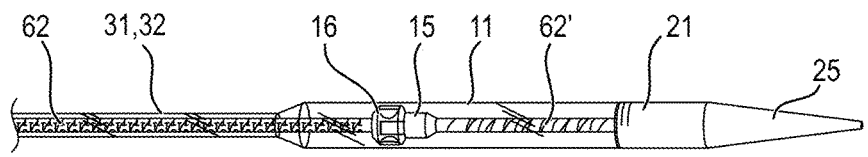
Figure 13B:
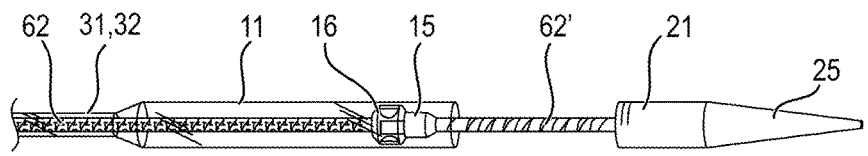
Figure 13C:
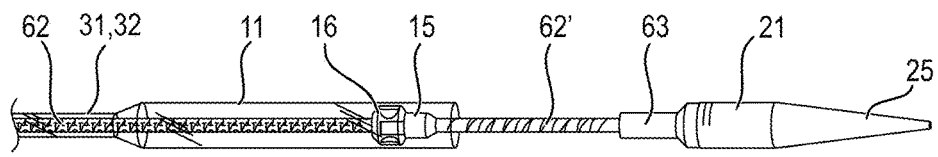
Figure 13D:
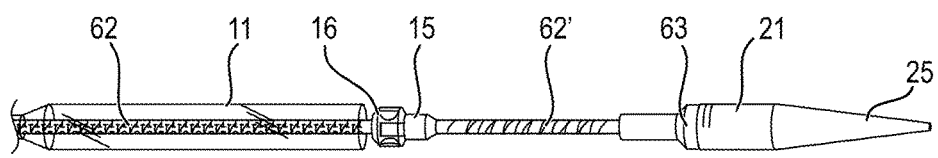
Figure 13E:
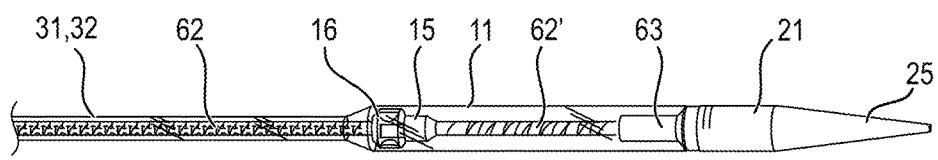

Of these:

FIG. 1: an embodiment of an insertion system for transfemoral/transarterial insertion of an expandable heart valve stent in a part-sectioned side elevation;

FIG. 2: an embodiment of a handle for an insertion system for transfemoral/transarterial insertion of an expandable heart valve stent in a part-sectioned side elevation;

FIG. 3*a*: an embodiment of an insertion system for transfemoral/transarterial insertion of a heart valve stent in a side elevation;

FIG. 3*b*: a side elevation of the transfemoral/transarterial insertion system in accordance with FIG. 3*a* with a deflected catheter system;

FIG. 4: a further embodiment of an insertion system for transfemoral/transarterial insertion of a heart valve stent in a side elevation;

FIG. 5: a further embodiment of an insertion system for transfemoral/transarterial insertion of a heart valve stent in a side elevation;

FIG. 6*a-d*: side elevations of the transfemoral/transarterial insertion system in accordance with FIG. 3*a* in its four previously defined functional states to illustrate the loading procedure of the insertion system FIG. 7*a-d*: side elevations of the transfemoral/transarterial insertion system in accordance with FIG. 3*a* in its four previously defined functional states to illustrate the release procedure of a stent housed in the catheter tip of the insertion system;

FIG. 8: an embodiment of a catheter tip for an insertion system for transfemoral/transarterial insertion of an expandable heart valve stent in a part-sectioned side elevation;

FIG. 9: a further embodiment of a catheter tip for an insertion system for transfemoral/transarterial insertion of an expandable heart valve stent in a part-sectioned side elevation;

FIG. 10*a*: an exemplary embodiment of a catheter shaft for an insertion system for transfemoral/transarterial insertion of an expandable heart valve stent in a cross-sectional elevation;

FIG. 10*b*: a further exemplary embodiment of a catheter shaft for an insertion system for transfemoral/transarterial insertion of an expandable heart valve stent in a cross-sectional elevation;

FIG. 11: a schematic view to illustrate a transfemoral transarterial implantation procedure of a heart valve stent;

FIG. 12*a-c*: three-dimensional schematic part-sectioned view of the catheter tip of a transfemoral/trans-apical insertion system in different functional states to illustrate the implantation procedure of a heart valve stent mounted in the catheter tip;

FIG. 13*a-d*: side elevations of a further embodiment of a catheter tip for an insertion system for transfemoral j transarterial insertion of an expandable heart valve stent in its four previously defined functional states to illustrate the release procedure of a stent housed in the catheter tip of the insertion system; and FIG. 13*e*: a side elevation of the embodiment of a catheter tip in accordance with FIG. 13*a-d* in its state after releasing a stent housed in the catheter tip and ready to be removed again from the body of the patient.

FIG. 11 shows schematically an example of how a transarterial or transfemoral access can be gained to the heart of a patient. In the illustration in accordance with FIG. 11, a heart valve stent 150 is advanced with the aid of a insertion system 100 via the femoral artery to the aortic valve. Embodiments of an insertion system 100, which is suitable for transarterial or transfemoral access, are described in the following.

In accordance with a preferred embodiment, an insertion system 100 has a catheter system 1 and a handle 70 connected to the proximal end section of the catheter system 1. As depicted, for example, in FIG. 1, the catheter system 1 of the preferred embodiment comprises a catheter tip 10 having a seat portion for accommodating a stent to be inserted in its collapsed state and a stent holder 15 for releasably fixing the stent. The catheter system 1 further comprises a catheter shaft 30 for connecting the catheter tip 10 to the handle 70 of the insertion system 100, the distal end section of the catheter shaft 30 being flexible enough such that the catheter tip 10 and the distal end section of the catheter shaft 30 may pass the aortic arch during insertion through the aorta of the patient.

The seat portion of the catheter tip 10 comprises a first sleeve-shaped member 11 and a second sleeve-shaped member 21, the cross-section of the second sleeve-shaped member 21 are preferably identical to each other such that the first and second sleeve-shaped member 11, 21 can completely enclosed a stent accommodated in the catheter tip 10. In addition, the first and second sleeve-shaped members 11, 21 are movable relative to each other and relative to the stent holder 15.

For this purpose, first force transmitting means 31 with a distal end section connected to the first sleeve-shaped member 11 and a proximal end section connected to first operating means 71 of the handle 70 are provided. In addition, second force transmitting means 41 with a distal end section connected to the second sleeve-shaped member 21 and a proximal end section connected to second operating means 81 of the handle 70 are provided. When manipulating the first and/or second operating means 71, 81 of the handle 70, the first and/or second sleeve-shaped members 11, 21 may be moved relative to each other and relative to the stent holder 15.

As can be seen from FIG. 10*a* and FIG. 10*b*, the first force transmitting means 31 may be constituted by a first catheter tube 32 defining a first lumen and the second force transmitting means 41 is constituted by a second catheter tube 42 defining a second lumen. The second catheter tube 42 may have a cross-section less than the cross-section of the first catheter tube 32. The first catheter tube 32 may be disposed concentrically and coaxially with the second catheter tube 42 and the second catheter tube 42 is received within the first lumen defined by the first catheter tube 32.

Contrary to the first and second sleeve-shaped members 11, 21 of the catheter tip 10, however, the stent holder 15 of the catheter tip 10 is not moveable relative to the handle 70 of the insertion system 100. Rather, the stent holder 15 is connected to the housing 70' of the handle 70 by using a stent holder tube 62 having a distal end connected to the stent holder 15 and a proximal end connected to a body 70' of the handle 70.

Referring to FIG. 10*b*, the stent holder tube 62 may have a cross-section less than the cross-section of the first catheter tube 32. In particular, the first catheter tube 32 may be disposed concentrically and coaxially with both, the second catheter tube 42 on the one hand and the stent holder tube 62 on the other hand. Preferably, the stent holder tube 62 has a cross-section less than the cross-section of the first catheter tube 32 and greater than the cross-section of the second catheter tube 42 such that the stent holder tube 62 is received within the first lumen defined by the first catheter tube 32 and the second catheter tube 42 is received within a passageway defined by the stent holder tube 62. The passageway defined by the stent holder tube 62 has a diameter sufficient to accommodate the second catheter tube 42 such that the second catheter tube 42 is moveable relative to the stent holder tube 62.

The second lumen defined by the second catheter tube 42 has a diameter sufficient to accommodate a guide wire 180. The second catheter tube 42 may be made from a rigid material including, for example, nitinol, stainless steel or a rigid plastic material (see FIG. 10*b*). The material of the distal end section of the second catheter tube 42 may have an increased flexibility compared to the material of the proximal end section in order to allow the distal end section of the catheter shaft 30 to pass the aortic arch during insertion of the catheter tip 10. For example, the guiding tube 52 may be a 17F-catheter tube and the first catheter tube 32 may be a 12F-catheter tube.

As can been seen, for example, from FIG. 9, the distal end section of the second catheter tube 42 terminates in a soft catheter end tip 25 having an atraumatic shape. The soft catheter end tip 25 is provided with a channel aligned with the second lumen defined by the second catheter tube 42 such that a guide wire 180 accommodated within the second lumen of the second catheter tube 42 may pass through the channel of the soft catheter end tip 25. The second sleeve-shaped member 21 of the catheter tip 10 is connected to the soft catheter end tip 25 such that the opened end of the second sleeve-shaped member 21 faces in the proximal direction opposite to the direction of the soft catheter end tip 25 and to the second catheter tube 42.

According to the exemplary embodiment depicted in FIG. 10*b*, the stent holder tube 62 is made of a rigid material, for example, a rigid plastic material, stainless steel or nitinol. The distal end of the stent holder tube 62 terminates in the stent holder 15 which is also made of a rigid material, for example, a rigid plastic material or stainless steel. The passageway defined by the stent holder tube 62 is aligned with a channel which passes through the stent holder 15. In this way, the second catheter tube 42 is accommodated in the passageway of the stent holder tube 62 and the channel of the stent holder 15 such as to be moveable relative to the stent holder tube 62 and the stent holder 15.

The first catheter tube 32 is made of a bendable but inelastic material. For example, the first catheter tube 32 may be at least partly made of a braided or non-braided catheter tube. The first catheter tube 32 shall be adapted to transfer compression and tension forces from the first operating means 71 of the handle 70 to the first sleeve-shaped member 11 of the catheter tip 10 without overly changing its total length. The distal end of the first catheter tube 32 terminates at a flared section as a transition to the section defining the first sleeve-shaped member 11 of the catheter tip 10.

As can be seen from FIG. 9, the flared section and the first sleeve-shaped member 11 may be formed integrally and may be connected to the distal end section of the first catheter tube 31. In addition, the flared section may constitute the first sleeve-shaped member 11 of the catheter tip 10. The first sleeve-shaped member 11 and the flared section of the first catheter tube 31 may be all of the same material and originating from the same raw tube prior to a widening process so that the flared section and the first sleeve-shaped member 11 are the same elements.

Referring for example to FIG. 1, the insertion system 100 according to the preferred embodiment further comprises a guiding tube 52 having a cross-section greater than the cross-section of the first catheter tube 32. The guiding tube 52 defines a passageway and is disposed concentrically and coaxially with the first catheter tube 32, the stent holder tube 62 and the second catheter tube 42 such that the first catheter tube 32 with the stent holder tube 62 and the second catheter tube 42 accommodated therein is at least partly accommodated within the passageway defined by the guiding tube 52, wherein the first catheter tube 32 is moveable relative to the guiding tube 52. In particular, the guiding tube 52 terminates proximal to the catheter tip 10 wherein the cross-section of proximal end section of the guiding tube 52 shall be the same as or less than the cross-section of the flared section provided at the proximal end of the first catheter tube 32 so that a smooth transition from the first sleeve-shaped member 11 of the catheter tip 10 to the guiding tube 52 may be achieved (see FIG. 9).

The proximal end section of the guiding tube 52 terminates distal to the handle 70. The proximal end section of the guiding tube 52 may be detached/disconnected from the handle 70 so that the handle 70 as well as the first and second catheter tubes 32, 42 and the stent holder tube 62 together with catheter tip 10 may be moved relative to the guiding tube 52.

The distal end of the guiding tube 52 is formed such that the flared section provided at the distal end section of the first catheter tube 32 may abut on the distal end of the guiding tube 52 without abrupt transition. The guiding tube 52 may be of a thin material such as to allow length deformation of the guiding tube 52 upon transfer of compression and tension forces. The material of the guiding tube 52, however, shall have sufficient stiffness in order to mechanically avoid kinking of the flexible sections of the distal portion of the catheter shaft 30 during insertion of the catheter tip 10.

The proximal end of the guiding tube 52 is releasably connectable to the body 70' of the handle 70. In this way, the guiding tube 52 may have a double-function:

In case, the proximal end of the guiding tube 52 is connected to the handle 70, the guiding tube 52 serves as a distal extension of the body 70' of the handle 70 relative to which the first and second operating means 71, 81 are moveable for manipulating the first and second sleeve-shaped members 11, 21 of the catheter tip 10. Hence, the position of the stent holder 15 relative to the native heart valve of the patient may be changed by moving the guiding tube 52 connected to the handle 70.

In case, the proximal end of the guiding tube 52 is not connected to the body 70' of the handle 70, the guiding tube 52 may serve as an introducer tube, i.e. as a portal for passing the catheter tip 10 of the catheter system 1 into the patient's body and up to the heart.

As depicted, for example, in FIG. 1, an inlet port 53 may be provided at a proximal end section of the guiding tube 52 for injection of fluids into the guiding tube 52. Furthermore, a check valve may be provided at the proximal end section of the guiding tube 52 to prevent fluid from leaking out of the guiding tube 52.

A description is given in the following, with reference to FIGS. 1 to 10b, of the components of exemplary embodiments of insertion systems 100, which are suitable for a transarterial or transfemoral access to the implantation location. During a transarterial or transfemoral access, the catheter tip 10 of the insertion system 100 is advanced, for example, via the aorta to the implantation site.

FIG. 1 shows a part-sectioned representation of an exemplary embodiment of an insertion system 100 designed for transfemoral or transarterial access.

As illustrated in FIG. 1, an insertion system 100 according to the present disclosure may comprise a catheter system 1 and a handle 70 connected to the proximal end section of the catheter system 1. The catheter system 1 comprises a catheter tip 10 and a catheter shaft 30 for connecting the catheter tip 10 to the handle 70. The catheter tip 10 has a seat portion for accommodating a stent (see FIGS. 12a-c) in its collapsed state as well as a stent holder 15 for releasably fixing the stent.

The seat portion of the catheter tip 10 is constituted by a first sleeve-shaped member 11 and a second sleeve-shaped member 21. As will be explained in more detail with reference to FIGS. 6a-d and FIGS. 7a-d, the sleeve-shaped members 11, 21 of the catheter tip 10 are movable relative to each other and relative to the stent holder 15.

The catheter shaft 30 comprises first force transmitting means 31, second force transmitting means 41 and guiding means 51. In accordance with the exemplary embodiment depicted in FIG. 1, the first and second force transmitting means 41 31, 41 of the catheter system 1 are realized as flexible, elongated catheter tubes 32, 42. Each of the first and second catheter tubes 32, 42 defines a separate lumen. In addition, the guiding means 51 is realized as guiding tube 52 defining a passageway within which the first and second catheter tubes 32, 42 are received such as to be movable relative to the guiding tube 52.

As can be seen in FIG. 1, the guiding tube 52 has a distal end which terminates proximal to the catheter tip 10. On the other hand, the first catheter tube 32 has a length which is the same as, or substantially similar to the length of the second catheter tube 42. The first catheter tube 32 terminates at its distal end in a flared section as a transition to the section with wider cross-section defining the first sleeve-shaped member 11 of the catheter tip 10. In particular, and as can be seen from the illustration in FIG. 9, the wider section of the first catheter tube 32 is formed integrally with the distal end section of the first catheter tube 32. The wider section has a length greater than the length of a collapsed stent to be accommodated in the catheter tip 10.

As already mentioned, in the exemplary embodiment depicted in FIG. 1, the first force transmitting means 31 of the catheter system 1 is constituted by a first catheter tube 32 defining a first lumen, wherein the second force transmitting means 41 is constituted by a second catheter tube 42 defining a second lumen. The second catheter tube 42 has a cross-section less than the cross-section of the first catheter tube 32, wherein the first catheter tube 32 is disposed concentrically and coaxially with the second catheter tube 42. The cross-section of the catheter tip 10, however, is greater than or equal to the cross-section of the guiding tube 52.

On the other hand, the guiding tube 52 has a cross-section which is greater than the cross-section of the part of the first catheter tube 32 which is received within the guiding tube 52. The cross-section of the catheter tip 10, however, is greater than the cross-section of the guiding tube 52. Hence, the guiding tube 52 cannot be removed from the insertion system 100 without disconnecting the catheter system 1 from the handle 70.

At the proximal end section of the guiding tube 52, a check valve may be provided for preventing fluid from leaking out of the guiding tube 52. Furthermore, an inlet port 53 may be provided at the proximal end section of the guiding tube 52 for injection of fluids into the guiding tube 52. Hence, fluids such as saline solution may be injected through the inlet port 52 to flush the interior passageway of the guiding tube 52 and to reduce the incidence of blood clotting. A stopcock may be attached to the inlet port 53 to maintain the port 53 in a closed position when the port 53 is not being accessed to flush the passageway of the guiding tube 52.

The guiding tube 52 is movable relative to the handle 70 and the first and second catheter tubes 32, 42. This provides a grip for the user who can hold the catheter shaft 30 at its proximal end section during positioning of the catheter tip 10 and during manipulation of the sleeve-shaped element 11 of the catheter tip 10. The user can hold the guiding tube 52, and in particular the proximal end section of the guiding tube 52 for supporting the movement of the first sleeve-shaped element 11 of the catheter tip 10 relative to the handle 70 such that the outer sheath of the catheter system 1 need not be held by the user or kinked.

In the exemplary embodiment of the insertion system 100 depicted in FIG. 1, a handle 70 is utilized, said handle 70 comprising first and a second operating means 71, 81, which are connected by means of corresponding first and second force transmission means 31, 41 of the catheter shaft 30 to the first and second sleeve-shaped member 21s 11, 21 of the catheter tip 10. The first operating means 71 has a first pusher 73 which is functionally connected to the first slide 74. The first slide 74 is guided in a first guide 72 in the longitudinal direction L of the handle 70. The distal-side end of the first guide 72 defines the first stop 75 and the proximal-side end of the first guide 72 the second stop 76, which define the overall longitudinal displacement that can be effected with the first operating means 71. A locking element 77' may be positioned between the distal-side and the proximal-side end of the first guide 72, which defines the additional stop 77.

The second operating means 81 of the handle 70 shown in FIG. 1 has a second pusher 83, which is functionally connected to a second slide 84. The second slide 84 is guided in a longitudinal guide (second guide 82) between a first stop 85 and a second stop 86. The second slide 84 is connected by means of the second force transmission means 41 with the second sleeve-shaped member 21 of the catheter tip 10. On actuation of the second operating means 81, the second slide 84 is moved in the longitudinal direction L of the handle 70 from the first stop 85 to the second stop 86. This movement effects a longitudinal displacement of the second sleeve-shaped member 21 of the catheter tip 10 connected via the second force transmission means 41 with the second operating means 81.

To prevent an unintended displacement of the second slide 84, the second operating means 81 is equipped with a securing element 89, which may connect the second slide 84 with the body 70' of the handle 70 when in use. A longitudinal displacement of the second slide 84 to the second stop 86 is possible following removal or deactivation of the securing element 89.

FIG. 2 shows a further embodiment of a handle 70 of an insertion system 100 designed for transfemoral or transarterial access in a part-sectioned side view. The construction and mode of operation of the first and second operating means 81 71, 81 of the embodiment of the handle 70 shown in FIG. 2 is comparable in structural and functional respects to the handle 70 as previously described with reference to FIG. 1. Hence, elements in FIG. 2 that are generally similar to previously described elements have the same reference numbers compared with the reference numbers in FIG. 1 previously used for the similar elements.

In distinction to the handle 70 described with reference to FIG. 1, however, the handle 70 in accordance with FIG. 2 is provided with a third operating means 96 in the form of a wheel, by means of which a flexural link region 34 of the catheter shaft 30 can be controlled. It is important to note, however, that the catheter shaft 30 is only optionally provided with such flexural link region 34. Rather, the material of the distal end section of the catheter shaft 30 may have an increased flexibility compared to the material of the proximal end section in order to allow the distal end section of the catheter shaft to pass 30 the aortic arch during insertion of the catheter tip.

In the exemplary embodiment depicted in FIG. 2, the third operating element 96 preferably has a detent device 100', to allow a set deflection of the flexural link region 34 of the catheter shaft 30 to be fixed. For example, it is possible to provide a suitable catch mechanism on the hand wheel of the third operating means 96, which cooperates with the body 70' of the handle 70. In particular, it is possible for the flexural link region 34 of the catheter shaft 30 to be connected to the third operating means 96 by way of a control wire 35 whereby, on an actuation of the third operating means 96 via the control wire 35 a tensile forces is exerted on the flexural link region 34, which produces the deflection of the flexural link region 34 (see FIG. 3b).

However it is also possible, of course, to choose another embodiment as the third operating means 96 for deflecting a flexural link region 34 of the catheter shaft 30, in case the catheter shaft 30 is provided with such a flexural link region 34.

The handle 70 of the insertion system 100 designed for transarterial or transfemoral access may be provided with a pretensioning device, shown in FIG. 2. With such a pretensioning device, a constant tensile force may be exerted via the second operating means 81 on the second sleeve-shaped member 21 of the catheter tip 10. As shown in FIG. 2, the pretensioning device may have a compression spring 97, permanently stressed along its spring axis, which is prestressed between a first stop 97a connected to the body 70' of the handle 70 and a second stop 97b connected to the proximal end region of the second operating means 81. In this respect, a permanent, previously defined or definable tensile force is exerted on the second sleeve-shaped member 21 of the catheter tip 10.

The pretensioning device implemented with the spring 97 in the embodiment in accordance with FIG. 2 may be advantageous when the catheter shaft 30 is bent during the implantation procedure, for example, when the catheter tip 10 of the insertion system 100 is inserted through the aorta. When the catheter shaft 30 is bent, the outer fibres of the catheter shaft 30 are shortened. This can be compensated appropriately with the aid of the pretensioning device. In detail, on bending of the flexural link region 34 relative to the neutral fibres of the catheter shaft 30 running along the longitudinal axis L, the outer fibres of the catheter shaft 30 radially spaced from the neutral fibres are shortened. Since the second force transmission means 41, which connects the second operating means 81 with the second sleeve-shaped member 21 in the insertion system 100, normally runs along the neutral fibre of the catheter shaft 30, a bending contraction inevitably occurs when the catheter shaft 30 is bent, having the result that, despite fixing of the first operating means 71, the first sleeve-shaped member 11 of the catheter tip 10 is displaced relative to the stent holder 15 in a proximal direction.

This longitudinal displacement of the first sleeve-shaped member 11 of the catheter tip 10 that takes place during the bending procedure is compensated with the aid of the prestressing device (spring 97), since the spring 97 of the prestressing device exerts a constant tensile force on the second force transmission means 41 and therefore on the second sleeve-shaped member 21 of the catheter tip 10 and consequently constantly presses the distal-side end tip 25 of the catheter tip 10 against the distal-side end of the first sleeve-shaped member 11. This enables the catheter tip 10 to remain completely closed even during a deflection of the catheter shaft 30 effected, for example, when the catheter tip 10 is inserted through the aorta.

On actuation of the second operating means 81 of the handle 70, it is necessary to press the second slide 84 against the prestress supplied by the spring 97 of the prestressing device on the second stop 86.

It is important to note, however, that a prestressing device of the kind as described above is not mandatory for the insertion system as disclosed herein.

A further exemplary embodiment of an insertion system 100 designed for transarterial/transfemoral access is shown in FIGS. 3*a*, *b*. Elements in FIGS. 3*a*, *b* that are generally similar to previously described elements have the same reference numbers compared with the reference numbers in FIGS. 1 and 2 previously used for the similar elements.

The insertion system 100 shown in FIGS. 3*a*, *b* comprises a catheter system 1 of the kind as previously described with reference to FIG. 1, i.e. a catheter system 1 having a catheter tip 10 and a catheter shaft 30 which is provided with a first catheter tube 32 acting as first force transmitting means 31, a second catheter tube 42 acting as second force transmitting means 41, and a guiding tube 52 acting as guiding means 51. Contrary to the catheter shaft 30 utilized in the exemplary embodiment of the insertion system 100 depicted in FIG. 1, however, the catheter shaft 30 of the insertion system 100 shown in FIGS. 3*a*, *b* is provided with a flexural link region 34 of the kind as previously described with reference to FIG. 2.

As will be described in the following, the insertion system 100 shown in FIGS. 3*a*, *b* is provided with a different embodiment of a handle 70 which is used in order to manipulate the first and second sleeve-shaped members 11, 21 of the catheter tip 10.

In relation to the handle 70 used with the insertion system 100 shown in FIG. 3*a*, it can be seen that the end region of the handle 70 is in the form of a turning mechanism 98 (rotatable means), with which the second force transmission means 41 of the catheter shaft 30 can be twisted with the distal-side end tip 25 and the second sleeve-shaped member 21 of the catheter tip 10 fastened to it about the longitudinal axis L of the catheter tip 10. The second sleeve-shaped member 21 of the catheter tip 10 is connected by means of a loose bearing to the stent holder 15, allowing transmission of a turning moment between the second sleeve-shaped member 21 and the stent holder 15, without allowing transmission of any tensile or compression forces acting in the direction of the longitudinal axis L of the catheter tip 10. Thus, when a turning movement of the second sleeve-shaped member 21 is induced with the turning mechanism 98, the stent holder 15 also turns correspondingly about the longitudinal axis L.

The turning mechanism 98 preferably allows the stent holder 15 to twist through approximately 120°. Thus the rotation of a stent housed in the catheter tip 10, and particularly the positioning hoops already released in the second functional state of the insertion system 100, can be controlled, facilitating precise positioning of the already expanded positioning hoops of the stent in the pockets of the insufficient, native heart valve.

Preferably, the rotation movement of the stent holder 15 about the longitudinal axis L of the catheter tip 10 that can be effected with the turning mechanism 98 exhibits a previously definable, preferably small delay in reaction to a turning moment initiated by means of the turning mechanism 98.

Further, the embodiment of the handle 70 shown in FIG. 3*a* is equipped with a third operating means 96 in the form of a wheel, with which a flexural link 34, preferably provided at the distal end region of the catheter shaft 30, can be deflected.

The deflection of the distal end region of the catheter shaft 30 that can be effected with this flexural link region 34 is shown schematically in FIG. 3*b*. In detail, a device is provided for force transmission (control wire 35—see FIG. 8) which is connected on one side to the flexural link regions 34 preferably provided at the distal end region of the catheter shaft 30 and, on the other side, to the third operating means 96 of the handle 70 implemented in the embodiment shown in FIG. 3 as a hand wheel.

It is possible to implement the device for force transmission as a control wire 35, which is passed through the inside of the first transmission means 31 and preferably at the distal end of the flexural link region 34 or at the proximal end of the catheter tip 10 (see FIG. 8) to have a directed effect on the curvature of the flexural link region 34. With the tensile forces that can be exerted on the flexural link region 34 with the aid of the control wire 35, it is possible to obtain a defined curvature of the distal end region of the catheter shaft 30. This is a particular advantage during transarterial/transfemoral access when navigating the aortic arch.

Further exemplary embodiments of an insertion system 100 which is suitable for transarterial/transfemoral access to the implantation location are shown in FIGS. 4 and 5. Elements in FIGS. 4 and 5 that are generally similar to previously described elements have the same reference numbers compared with the reference numbers in FIGS. 1, 2 and 3*a*, *b* previously used for the similar elements.

Compared with the exemplary embodiment depicted in FIGS. 1 and 2 as well as FIGS. 3*a*, *b*, the embodiments shown in FIGS. 4 and 5 differ first and foremost in relation to the implementation of the corresponding operating means 71, 81 of the handle 70.

The insertion system 100 in accordance with FIG. 4 has a handle 70 with which the first operating means 71, which is used for manipulation of the first sleeve-shaped member 11 of the catheter tip 10, is similar to a trigger of a revolver. The user such as a physician who carries out the treatment may hold the handle 70 at the grip 88, while the first operating means 71 in the form of a trigger of a revolver is operated with the index finger of the hand holding it.

In the insertion system 100 shown in FIG. 5, a handle 70 is used which corresponds in structural and functional respects to the handle 70 used with the insertion system 100 in FIG. 3 with the exception of the grip 88 provided in the embodiment in accordance with FIG. 3.

A description is given in the following, with reference to FIGS. 6*a-d* and FIGS. 7*a-d*, of the functional coaction of the components of an insertion system 100, which is suitable for a transarterial or transfemoral access to the implantation location. Elements in FIGS. 6*a* to 6*d* and FIGS. 7*a* to 7*d* that are generally similar to previously described elements have the same reference numbers compared with the reference numbers in FIGS. 1 to 5 previously used for the similar elements.

Reference is made to FIGS. 6*a* to 6*d* for illustrating the procedure for loading a stent into the catheter tip 10 of the insertion system 100. In FIGS. 7*a* to 7*d*, the stepwise release of a stent mounted in the catheter tip 10 of the insertion system 100 is illustrated.

It is important to note, however, that the procedure for loading a stent into the catheter tip 10 as depicted in FIGS. 6*a* to 6*d*, as well as the procedure for stepwise releasing of a stent mounted in the catheter tip 10 as depicted in FIGS.

7a to 7d also apply to the other exemplary embodiments of the transarterial/transfemoral insertion system 100 disclosed herein.

The handle 70 for the transarterial/transfemoral insertion system 100 according to the illustration in FIGS. 6 and 7 has a wheel rotatably mounted in the handle 70 which is functionally connected to the first sleeve-shaped member 11 of the catheter tip 10 associated with the first operating means 71 via a corresponding first force transmission means 31, so that force can be directly transmitted from the first operating means 71 in the form of the wheel to the first sleeve-shaped member 11 of the catheter tip 10.

In detail, it is provided that, with the first operating means 71 of the handle 70 in accordance with FIG. 6 and FIG. 7, the first operating means 71 in the form of the wheel can turn between a first stop and a second stop, in order to execute a definable longitudinal displacement stroke on the first sleeve-shaped member 11 of the catheter tip 10. The first operating means 71 of the handle 70 is provided with a additional stop between the first and second stop which cooperates, on one side with the first stop and on the other up with the second stop so that, on actuation of the first operating means 71, a longitudinal displacement of the first sleeve-shaped member 11 of the catheter tip 10 can be effected relative to the stent holder 15 of the catheter tip 10, consisting of two defined separate steps.

With the first operating means 71 used in the form of a wheel, the additional stop associated with the first operating means 71 is in the form of a locking element 77' positioned removably in the flow of force between the wheel and the first sleeve-shaped member 11 of the catheter tip 10, interrupting direct force transmission from the wheel to the first sleeve-shaped member 11 of the catheter tip 10. Alternatively, however, it is possible for the additional stop associated with the first operating means 71 to be in the form of a locking element restricting the free rotation of the wheel between the first and the second stop.

However, it is of course also possible in principle for the first operating means 71 of the handle 70 used with the insertion system 100 designed for transarterial/transfemoral access not to be a wheel, but to be implemented as a pusher mechanism.

In relation to the handle 70 that is used with the embodiment of the insertion system 100, for example in accordance with the illustrations in FIGS. 6 and 7, it is provided that the second operating means 81 has a second slide 84 guided in a second guide 82 and functionally connected to a second pusher 83. This second slide 84, which is guided in the interior of the handle 70 and therefore cannot be seen in the view of FIGS. 6 and 7, is functionally connected to the second sleeve-shaped member 21 of the catheter tip 10 associated with the second operating means 81 by means of a second force transmission means 41 so that, on actuation of the second operating means 81, force is directly transmitted from the second slide 84 to the second sleeve-shaped member 21 of the catheter tip 10.

The second operating means 81 can be displaced between a first position (Pos. 1) and a second position (Pos. 2) in the longitudinal direction of the handle 70, whereby the longitudinal displacement stroke that can be thus effected via the second force transmission means 41 is transferred directly to the second sleeve-shaped member 21 of the catheter tip 10. The first and second positions are each defined with the aid of a first and a second stop 85, 86.

A securing element 89 is provided, associated with the second operating means 81, which is removably located on the second guide 82 and which blocks longitudinal displacement of the (second) slide 84 associated with the second operating means 81 when used.

The handle 70 which is used with the transarterial/transfemoral insertion system 100 of the embodiment shown in FIGS. 6 and 7 further exhibits an optional grip 88, which facilitates the operability of the handle 70 and in particular the operating conformity of the handle 70. The grip 88 is preferably releasably connected to the body 70' of the handle 70 and can optionally be fixed at different positions on the body 70' of the handle 70.

In relation to the construction of the catheter tip 10 which is used, for example, with the insertion system 100 shown in FIGS. 6 and 7 and which allows transarterial/transfemoral access of a stent housed in the catheter tip 10 to the implantation location, it can be seen from FIGS. 6 and 7 that the catheter tip 10 has a stent holder 15 for releasably fixing of, for example, the second retaining region of a stent that can be housed in the catheter tip 10. The retaining elements 16 of the stent holder 15 in the form of a crown are provided at the proximal end of the stent holder 15.

Further, the catheter tip 10 of the insertion system 100 designed for transarterial/transfemoral access comprises a mounting device for mounting a heart valve stent, where required, with a heart valve prosthesis fastened to it. In detail, the mounting device of the catheter tip 10 consists of a first sleeve-shaped member 11, particularly for accommodating the positioning hoops of a stent, and a second sleeve-shaped member 21, in particular for accommodating the heart valve prosthesis fastened to it, when required.

The first operating means 71 of the handle 70 co-operates in the embodiment according to FIGS. 6 and 7 with the first sleeve-shaped member 11 of the catheter tip 10 so that, on actuation of the first operating means 71, by transfer of a defined longitudinal displacement stroke, a previously definable longitudinal displacement of the first sleeve-shaped member 11 can be effected relative to the stent holder 15. On the other hand, with the insertion system 100 according to FIGS. 6 and 7, the second operating means 81 of the handle 70 co-operates with the second sleeve-shaped member 21 of the catheter tip 10 so that, on actuation of the second operating means 81, by transfer of a defined longitudinal displacement stroke, a previously definable longitudinal displacement of the second sleeve-shaped member 21 of the catheter tip 10 relative to the stent holder 15 can be effected.

The second sleeve-shaped member 21, which is used to house the retaining hoops of the stent with, where required, the heart valve prosthesis fastened to them, is located at the distal end region of the catheter tip 10, while the first sleeve-shaped member 11 is located between the second sleeve-shaped member 21 and the handle 70.

In the insertion system 100 shown in FIGS. 6 and 7, the second force transmission means 41, which connects the second operating means 81 of the handle 70 to the second sleeve-shaped member 21 of the catheter tip 10, is preferably in the form of an inner catheter running inside the interior of the catheter or tube system. The first force transmission means 31, which connects the first operating means 71 of the handle 70 to the first sleeve-shaped member 11 of the catheter tip 10, is in the form of an outer catheter, in the interior of which the first force transmission means 31 runs in the form of the inner catheter.

On actuation on the second operating means 81, the second sleeve-shaped member 21 can be moved relative to the stent holder 15 in the longitudinal direction L of the catheter tip 10 in a distal direction, thus away from the handle 70, while, on actuation of the first operating means 71 of the handle 70, the first sleeve-shaped member 11 of the catheter tip 10 can be moved relative to the stent holder 15 in the longitudinal direction L of the catheter tip 10 in a proximal direction, and thus towards the handle 70.

The manipulations of the respective sleeve-shaped members 11, 21 of the catheter tip 10 that can be effected on actuation of the respective operating means 71, 81 with the insertion system 100 of 100 designed for transarterial/transfemoral access in accordance with FIGS. 6 and 7 are described in detail in the following, with reference in particular to FIGS. 7a to 7d.

An embodiment of a transarterial/transfemoral insertion system 100 is shown in its four different functional states in FIGS. 7a to 7d. In detail, the insertion system 100 is shown in its first functional state in FIG. 7a, in which the catheter shaft 30 with the catheter tip 10 and, where required, with the stent accommodated in it can be inserted into the patient transarterially or transfemorally and advanced via the aorta to the implantation site.

Figure 7A:
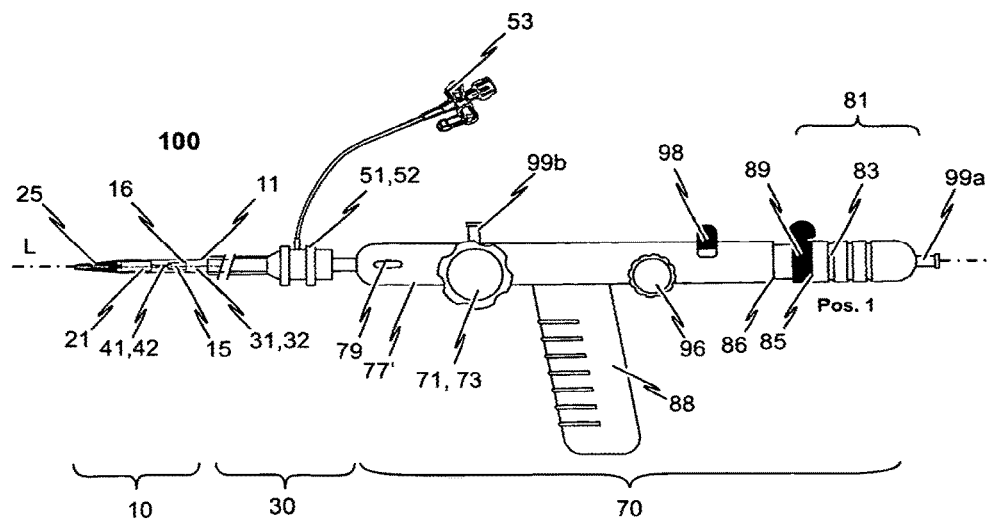

In the first functional state of the insertion system 100 in accordance with FIG. 7a, the catheter tip 10 is completely closed, whereby the two sleeve-shaped members 11, 21 of the catheter tip 10 overlap telescopically. The respective diameters of the sleeve-shaped members 11, 21 are chosen so that the folded-up retaining hoops of a stent, with the heart valve prosthesis fastened to them where required, can be housed in the second sleeve-shaped member 21. The folded-up positioning hoops of the stent housed between the second sleeve-shaped member 21 and the first sleeve-shaped member 11 are held together in their folded form.

The second retaining region of the stent is shown in the first functional state of the insertion system 100, as shown in FIG. 7a, with the stent holder 15 fixed at the proximal end of the catheter tip 10. For this purpose, the retaining elements (retaining rings etc.) provided at the second retaining region of the stent are engaged with retaining elements 16 of the stent holder 15.

The retaining elements 16 of the stent holder 15 are covered by the first sleeve-shaped member 11 of the catheter tip 10 in the first functional state shown in FIG. 7a, so that an engagement between retaining elements provided on the second retaining region of a stent and retaining elements 16 of the stent holder 15 would be possible.

The first functional state of the insertion system 100 shown in FIG. 7a is maintained during the transarterial insertion procedure. On reaching the implantation location, the insertion system 100 is transferred from the first functional state shown in FIG. 7a to the second functional state shown in FIG. 7b, by transferring the first operating means 71 (shown in the embodiment of the wheel in FIG. 7) from the first position into the second position. The longitudinal displacement stroke transferred by actuation of the first operating means 71 to the first sleeve-shaped member 11 of the catheter tip 10 effects a displacement of the first sleeve-shaped member 11 relative to the stent holder 15 in the proximal direction, thus towards the handle 70.

The longitudinal displacement stroke executed on the first sleeve-shaped member 11 of the catheter tip 10 during the transition from the first functional state (see FIG. 7a) to the second functional state (see FIG. 7b) by the first operating means 71 of the handle 70 via a corresponding first force transmission means 31 is previously defined so that the first sleeve-shaped member 11 is displaced relative to the stent holder 15 in the proximal direction just so far that the positioning hoops of a stent housed in the catheter tip 10 would be released, though the distal end of the first sleeve-shaped member 11 of the catheter tip 10 would still cover the retaining elements 16 of the stent holder 15, so that the engagement between the retaining elements provided at the second retaining region of the stent and the retaining elements 16 of the stent holder 15 would be secure.

Since the second sleeve-shaped member 21 is not manipulated during the transition from the first functional state into the second functional state, the first retaining region of a stent housed in the catheter tip 10 with the heart valve prosthesis fastened to it would continue to be housed in its folded together state in the sleeve-shaped element of the second sleeve-shaped member 21.

The positioning hoops of a stent housed in the catheter tip 10 released in the second functional state of the insertion system 100 are opened as a result of the radial forces acting on them and can thus be positioned in the pockets of the insufficient native heart valve. Following appropriate positioning of the positioning hoops of the stent in the pockets of the native heart valve, the insertion system 100 is transferred from the second functional state shown in FIG. 7b into the third functional state shown in FIG. 7c. This is done my manipulation of the second operating means 81, after the securing element 89 associated with the second operating means 81 has been removed.

On actuation of the second operating means 81, the second sleeve-shaped member 21 of the catheter tip 10 associated with the second operating means 81 is moved relative to the stent holder 15 by a previously established longitudinal displacement stroke defined with the second operating means 81 in a distal direction, thus away from the handle 70. The longitudinal displacement stroke acting on the second sleeve-shaped member 21 is chosen so that the sleeve-shaped member 21 no longer covers the first retaining region of a stent housed in the catheter tip 10 with the heart valve prosthesis fastened to it, where required, and thus releases the first retaining region of the stent. Due to the action of the radial forces, the distal retaining region of the stent with the heart valve prosthesis attached to it, where required, unfolds completely.

Figure 7B:
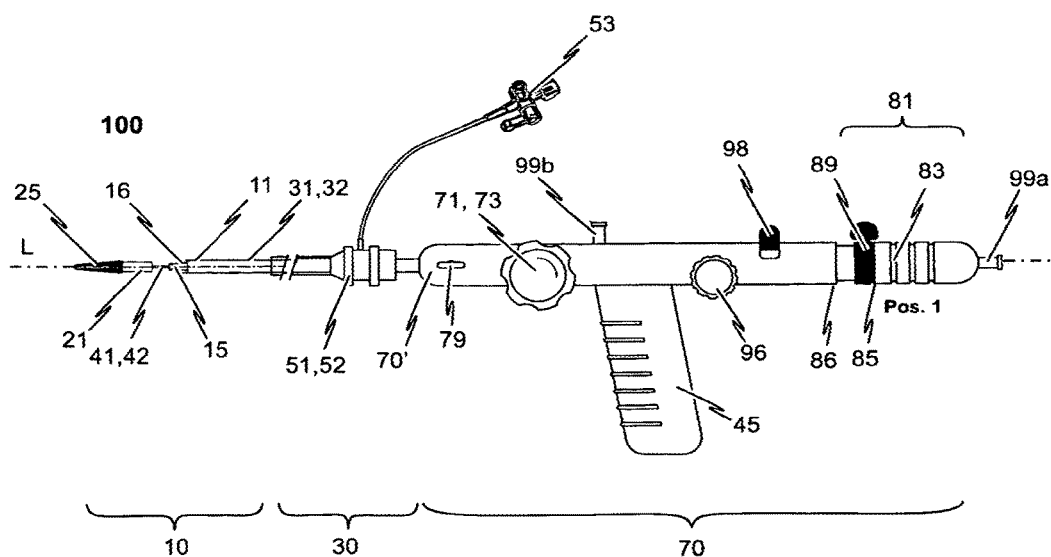
Figure 7C:
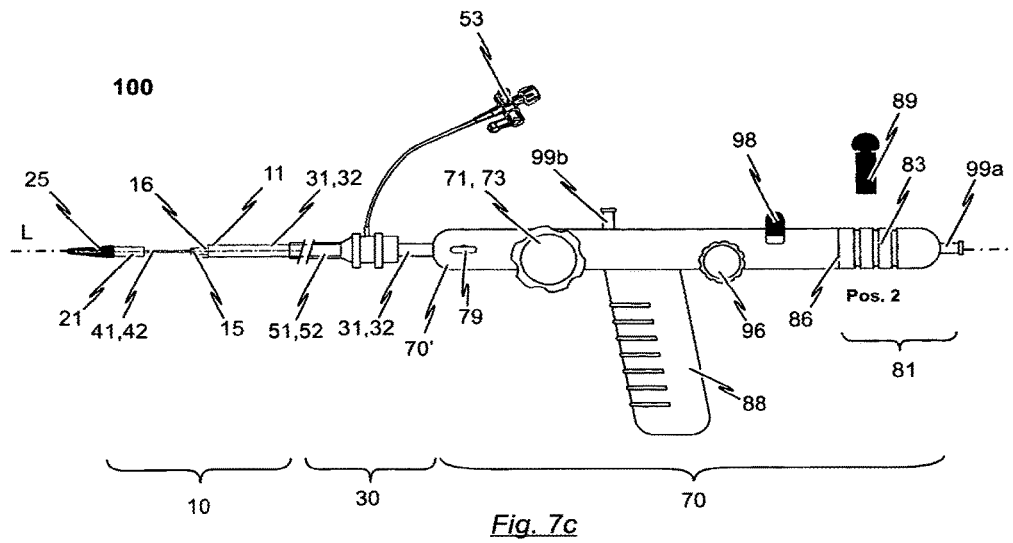

Since the first operating means 71 of the handle 70 and the associated first sleeve-shaped member 11 of the catheter tip 10 are not manipulated during the transition from the second functional state in accordance with FIG. 7b into the third functional state in accordance with FIG. 7c, the distal end region of the first sleeve-shaped member 11 continues to cover the retaining elements 16 of the stent holder 15, so that the engagement between the retaining elements of a stent housed in the catheter tip 10 and the retaining elements 16 of the stent holder 15 is secure and the proximal retaining region of the stent is in its folded-up state. This anchorage of the stent to the catheter tip 10 of the insertion system 100 allows an explantation of a stent that is already partially unfolded by returning the insertion system 100 from the third functional state, by appropriate manipulation of the second operating means 81 of the handle 70, to the second functional state and then by suitable actuation of the first operating means 71 transfer to the first functional state.

Figure 7D:
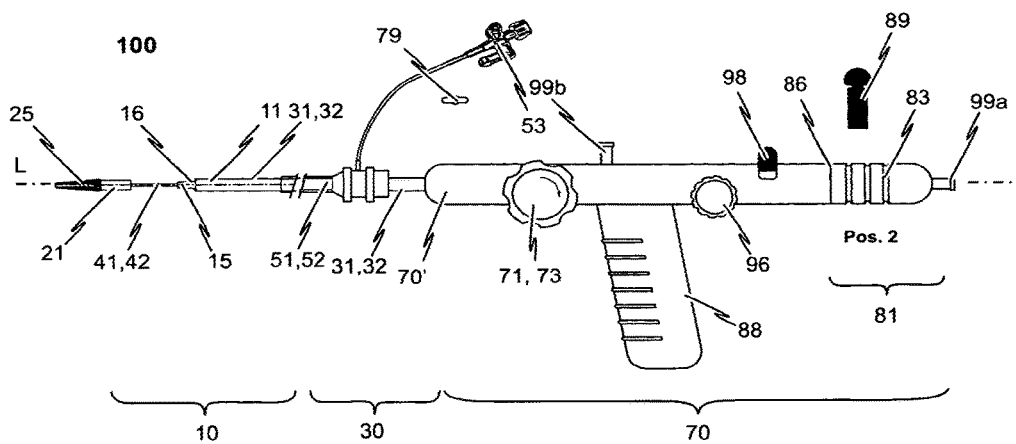

If an explantation of the stent with the heart valve prosthesis attached to it, where required, is unnecessary, the insertion system 100 is transferred from the third functional state shown in FIG. 7c into the fourth functional state shown in FIG. 7d, by turning the first operating means 71 of the handle 70 further from the second position to the third position after removal of the securing element 79 (locking element). This manipulation of the first operating means 71 that can be effected after removal of the securing element 79 results in a further defined movement of the first sleeve-shaped member 11 relative to the stent holder 15 of the catheter tip 10 in a proximal direction, thus towards the handle 70. The longitudinal displacement stroke executed on the first sleeve-shaped member 11 is chosen so that the distal end of the first sleeve-shaped member 11 no longer covers the retaining elements 16 of the stent holder 15, as a result of which an engagement between the retaining elements of a stent housed in the catheter tip 10 and the retaining elements 16 of the stent holder 15 can be released, which would also lead to a complete release of the second retaining region of the stent and a complete separation of the stent from the catheter tip 10 and correspondingly to a complete unfolding of the stent.

Figure 6A:
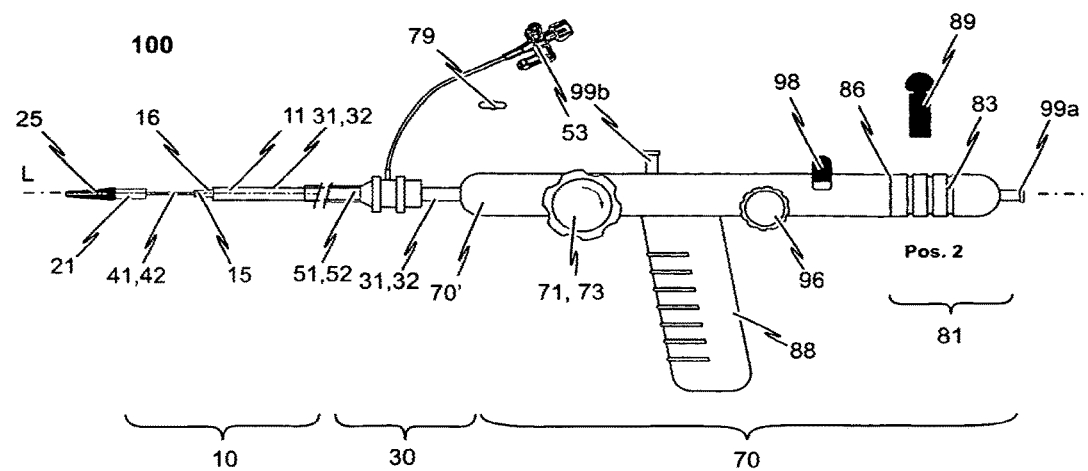
Figure 6B:
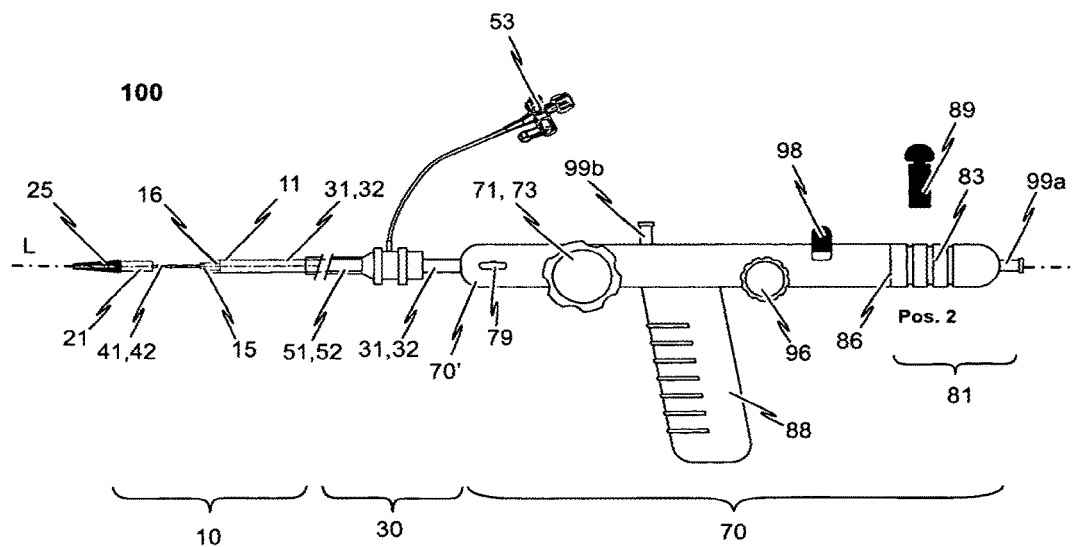
Figure 6C:
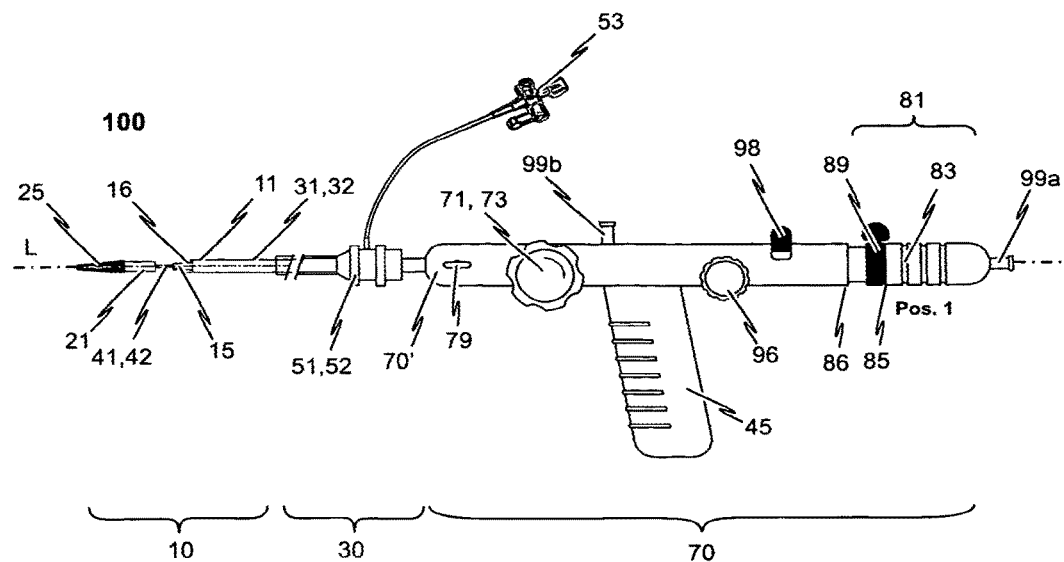
Figure 6D:
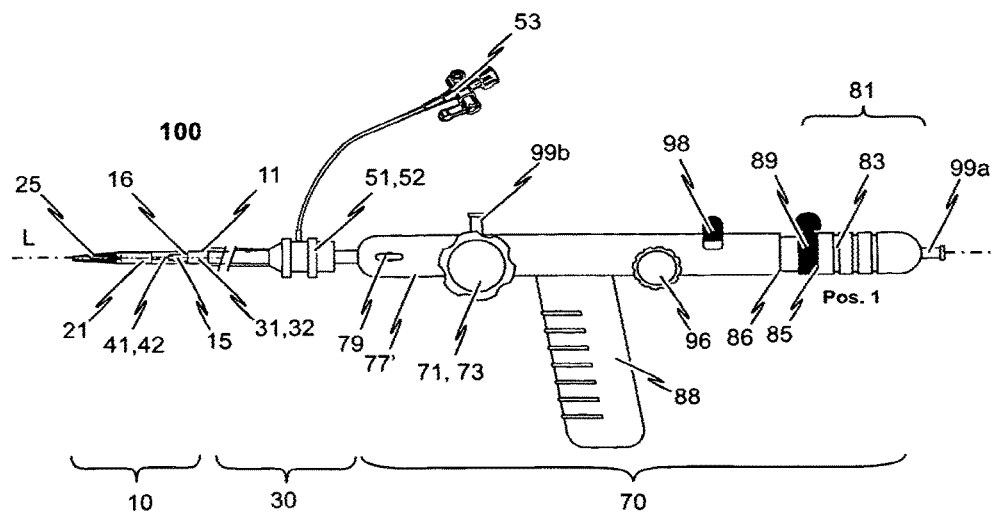

The four functional states of the insertion system 100 designed for transarterial/transfemoral access, previously described with reference to FIGS. 7a to 7d, are shown in reverse order in FIGS. 6a to 6d to clarify the procedure for loading a stent into the catheter tip 10 of the insertion system 100. Comparison between FIGS. 6a to 6d and FIGS. 7a to 7d show that the insertion system 100 can be loaded with a heart valve stent by transferring the insertion system 100, starting from its fourth functional state in accordance with FIG. 6a (see FIG. 7d), into its third functional state in accordance with FIG. 6b (see FIG. 7c) after a stent has been positioned between the stent holder 15 on the second sleeve-shaped member 21 with its first retaining region in the direction of the second sleeve-shaped member 21. Then the remaining functional states of the insertion system 100 are taken up in steps until the insertion system 100 shown in FIG. 6d is finally in its first functional state with the closed catheter tip 10.

Reference is made to FIG. 9 for describing an exemplary embodiment of the catheter tip 10. Elements in FIG. 9 that are generally similar to previously described elements have the same reference numbers compared with the reference numbers in FIGS. 1 to 7 previously used for the similar elements.

An exemplary embodiment of a catheter shaft 30 is described in the following, with reference to the illustration in FIG. 9. This catheter shaft 30 can be used with an insertion system 100 designed for transarterial or transfemoral access.

In detail, FIG. 9 shows an exemplary embodiment of a shaft for an insertion system 100 in a cross-sectional elevation.

The catheter shaft 30 exhibits a first force transmission means 31 in the form of a first catheter tube 32, whereby this first catheter tube 32 is used to connect the first operating means 71 of the handle 70 to the first sleeve-shaped member 11 of the catheter tip 10. As can be seen in particular from the illustration in FIG. 1, the first force transmission means 31 implemented as a first catheter tube 32 may be clamped between a screw cap 74' and the first slide 74 of the first operating means 71 and consequently is permanently connected to the first slide 74. The distal-side end region of the first catheter tube 32 merges into the first sleeve-shaped member 11 of the catheter tip 10 in the form of the stent sheath.

The second force transmission means 41 of the catheter shaft 30 used with an insertion system 100 designed for transarterial or transfemoral access is preferably implemented as a second catheter tube 42. The proximal-side end region of the second catheter tube 42 is connected to the second operating means 81 of the handle 70. The distal-side end region of the second catheter tube 42 is connected to the catheter end tip 25 of the catheter tip 10. The second sleeve-shaped member 21 of the catheter tip 10 is permanently connected by means of its distal-side end to the end tip 25 of the catheter tip 10 so that, on actuation of the second operating means 81 via the force transmission means 41 in the form of the second catheter tube 42, a tensile or compressive force can be transmitted to the second sleeve-shaped member 21 of the catheter tip 10.

The exemplary embodiment of the catheter tip 10 further comprises a stent holder 15 at the proximal end section of the catheter tip 10. The stent holder 15 has a passageway extending there through. The distal end section of the second force transmitting means 41 (second catheter tube 42) passes through the passageway of the stent holder 15 and terminates at the second sleeve-shaped member 21.

The respective sleeve-shaped members 11, 21 of the catheter tip 10 can be manipulated by corresponding operating means 71, 81 of a handle 70 (not shown in FIG. 9). In detail, the first sleeve-shaped member 11 of the catheter tip 10 is connected with a first operating means 71 of a handle 70 by using a first force transmitting means 31. On the other hand, the second sleeve-shaped member 21 of the catheter tip 10 is connected to a second operating means 81 of the handle 70 by using a second force transmitting means 41. In a preferred embodiment of the catheter shaft 30, the first force transmitting means 31 is constituted by a first catheter tube 32 defining a first lumen, wherein the second force transmitting means 41 is constituted by a second catheter tube 42 defining a second lumen. The second catheter tube 42 has a cross-section less than the cross-section of the first catheter tube 32, wherein the first catheter tube 32 is disposed concentrically and coaxially with the second catheter tube 42.

As shown in FIG. 9, the distal end section of the second catheter tube 42 passes through the opened front face of the second sleeve-shaped member 21 and terminates in a cone-shaped end tip 25 of the catheter system 1, wherein the base of this cone-shaped end tip 25 defines the distal front face of the second sleeve-shaped member 21.

The end tip 25 of the catheter system 1 is preferably a soft catheter end tip, for example a soft polymeric catheter end tip.

At its distal end, the first catheter tube 32 terminates after an intermediate flared section in a section with wider cross-section defining the first sleeve-shaped member 11 of the catheter tip 10. As can be seen from FIG. 9, the flared section is formed integrally with the distal end section of the first catheter tube 32. The flared section has a length greater than the length of a collapsed stent to be accommodated in the catheter tip 10, wherein the difference in the length between the flared section and the stent in its collapsed state represents the length of the stent holder 15.

The catheter shaft 30, which is connected to the catheter tip 10 depicted in FIG. 9, also comprises a guiding tube 52 of the kind as previously described with reference to the exemplary embodiment depicted in FIG. 1.

The distal end of the guiding tube 52 terminates proximal to the catheter tip 10. The guiding tube 52 defines a passageway within which the first and second catheter tube 42 32, 42 are received such as to be movable relative to the guiding tube 52.

The distal end of the guiding tube 52 may be tapered such that it abuts the first catheter tube 32 in one of its possible positions on the catheter shaft 30.

Reference is made to FIG. 10a, which is a cross-sectional view of a catheter shaft 30 according to an exemplary embodiment.

As can be seen from the illustration in FIG. 10a, the second force transmission means 41 in the form of the second catheter tube 42 runs along the neutral fibre of the catheter shaft 30 inside the first catheter tube 32. The space between the first catheter tube 32 and the second catheter tube 42 may be filled with a filler material, so that a filler body 40 is formed. The filler material is preferably a relatively elastic plastic material to allow the catheter shaft 30 to bend overall. The filler body 40 is used for connecting the stent holder 15 of the catheter tip 10 to the body 70' of the handle 70.

Alternatively, a stent holder tube 62 may be used for connecting the stent holder 15 of the catheter tip 10 to the body 70' of the handle 70. The stent holder tube 62 may have a distal end connected to the stent holder 15, a proximal end connected to the body 70' of the handle 70 and a passageway extending through the stent holder tube 62. Preferably, the stent holder tube 62 has a cross-section less than the cross-section of the first catheter tube 32 and greater than the cross-section of the second catheter tube 42, wherein the first catheter tube 32 is disposed concentrically and coaxially with the stent holder tube 62 thereby accommodating the stent holder tube 62 such that the first catheter tube 32 is moveable relative to the stent holder tube 62. The passageway of the stent holder tube 62 shall have a diameter sufficient to accommodate the second catheter tube 42 such that the second catheter tube 42 is moveable relative to the stent holder tube 62.

As depicted in FIG. 1, the filler body 40 (or the stent holder tube 62) may be connected by means of a fixing 87 to the body 70' of the handle 70. The proximal-side end region of the stent holder 15 attaches at the distal-side end region of the filler body 40 (see FIG. 8). The connection between the stent holder 15 and the filler body 40 is preferably chosen so that it allows rotation of the stent holder 15 relative to the filler body 40. This is especially necessary for control of the rotation of the positioning hoops of the already partially released stent during the implantation procedure (see FIG. 12a).

As an alternative, the complete catheter system 1 can be rotated for appropriate positioning of a stent connected with the catheter tip 10 and, in particular the positioning hoops of an already partially released stent during the implantation procedure. This is possible due to an appropriate transmission of torque and the flexibility of the catheter system 1.

In case, a stent holder tube 62 is used for connecting the stent holder 15 of the catheter tip 10 to the body 70' of the handle 70, the stent holder tube 62 may be rotatable relatively to the first and second catheter tubes 32, 42 about the longitudinal axis L of the catheter system 1. This will be described later in more detail with reference to the exemplary embodiment depicted in FIG. 10b.

On the other hand, the second force transmission means 41 in the form of the second catheter tube 42 can be turned about the longitudinal direction L, for example, by means of a rotatable cap 98 which may be provided at the proximal end region of the handle 70. This rotary movement is transferred from the second catheter tube 42 direct to the end tip 25 of the catheter tip 10 and thus to the second sleeve-shaped member 21 of the catheter tip 10.

It is particularly preferred that the second catheter tube 42 runs through the body of the stent holder 15 and cooperates with the stent holder 15 with the aid of a suitable toothing, to transmit a turning moment exerted by means of the rotary cap of the handle 70 on the second catheter tube 42 to the stent holder 15, while tensile or compression forces acting in the longitudinal direction L of the catheter tip 10 are not transmitted from the second catheter tube 42 to the stent holder 15.

As can also be seen in the illustration in FIG. 10a, a least one fluid channel 43 may be provided in the filler body 40 of the catheter shaft 30, connected at its proximal-side end to an injection adapter 99b (see FIG. 2) and at its distal-side end correspondingly to the catheter tip 10, consequently ensuring supply of fluid to the catheter tip 10 and draining of fluid from the catheter tip 10.

Furthermore, a channel may be provided in the filler body 40 for accommodating a control wire (control wire 35—see FIG. 8), with an operating means may cooperate with a flexural link region, in case the catheter shaft 30 is provided with such a flexural link region (see FIG. 3 and FIG. 2). In the illustration in FIG. 8, the distal-side end of a control wire 35 is fixed to the proximal-side end region of the stent holder 15.

Reference is made to FIG. 10b, which is a cross-sectional view of a catheter shaft 30 according to an alternative exemplary embodiment.

According to the embodiment depicted in FIG. 10b, the first force transmitting means 31 may be constituted by a first catheter tube 32 defining a first lumen and the second force transmitting means 41 is constituted by a second catheter tube 42 defining a second lumen. The second catheter tube 42 may have a cross-section less than the cross-section of the first catheter tube 32. The first catheter tube 32 may be disposed concentrically and coaxially with the second catheter tube 42 and the second catheter tube 42 is received within the first lumen defined by the first catheter tube 32.

A stent holder tube 62 is provided for connecting the stent holder 15 to the handle 70, said stent holder tube 62 having a distal end connected to the stent holder 15 and a proximal end connected to a body 70' of the handle 70.

As can be seen from FIG. 10b, the stent holder tube 62 may have a cross-section less than the cross-section of the first catheter tube 32. In particular, the first catheter tube 32 may be disposed concentrically and coaxially with both, the second catheter tube 42 on the one hand and the stent holder tube 62 on the other hand. Preferably, the stent holder tube 62 has a cross-section less than the cross-section of the first catheter tube 32 and greater than the cross-section of the second catheter tube 42 such that the stent holder tube 62 is received within the first lumen defined by the first catheter tube 32 and the second catheter tube 42 is received within a passageway defined by the stent holder tube 62. The passageway defined by the stent holder tube 62 has a diameter sufficient to accommodate the second catheter tube 42 such that the second catheter tube 42 is moveable relative to the stent holder tube 62.

The second lumen defined by the second catheter tube 42 has a diameter sufficient to accommodate a guide wire 180. The second catheter tube 42 may be made from a rigid material including, for example, nitinol, stainless steel or a rigid plastic material. The material of the distal end section of the second catheter tube 42 may have an increased flexibility compared to the material of the proximal end section in order to allow the distal end section of the catheter shaft 30 to pass the aortic arch during insertion of the catheter tip 10. For example, the guiding tube 52 may be a 17F-catheter tube and the first catheter tube 32 may be a 12F-catheter tube.

According to the exemplary embodiment depicted in FIG. 10b, the stent holder tube 62 is made of a rigid material, for example, a rigid plastic material, stainless steel or nitinol. The distal end of the stent holder tube 62 terminates in the stent holder 15 which is also made of a rigid material, for example, a rigid plastic material or stainless steel. The passageway defined by the stent holder tube 62 is aligned with a channel which passes through the stent holder 15. In this way, the second catheter tube 42 is accommodated in the passageway of the stent holder tube 62 and the channel of the stent holder 15 such as to be moveable relative to the stent holder tube 62 and the stent holder 15.

The embodiments of the insertion system 100 designed for transarterial/transfemoral access may have a first injection adapter 99a at the proximal end of the handle 70. This first injection adapter 99a is used for flushing the insertion system 100 and as outlet of a guide wire 180, with the aid of which the actual introduction of the catheter shaft 30 with the catheter tip 10 provided at the distal end of the catheter shaft 30 into the body of the patient is simplified. The catheter shaft 30, the catheter tip 10 and the handle 70 are thereby threaded into the guide wire 180 and pushed along it, for example into the aorta and to the heart of the patient.

In the embodiments of the insertion system 100 designed for transarterial/transfemoral access, a second injection adapter 99b may further be provided, by means of which a liquid coolant etc. can be passed, for example, via the fluid channels 43 (see FIG. 10a) formed in the interior of the catheter shaft 30 to the catheter tip 10. With the aid of such a liquid coolant, a stent accommodated in the catheter tip 10 can be appropriately cooled while the catheter tip 10 is being advanced to the implantation location, as long as the insertion system 100 is in its first functional state, in which the catheter tip 10 is completely enclosed by the telescopically arranged sleeve-shaped members 11 and 21.

The provision of cooling that can be produced with the second injection adapter 99b for the stent accommodated in the catheter tip 10 is a particular advantage when a shape memory material is used as stent material and when the stent can deform under the effect of an external stimulus from a temporary form to a permanent form, whereby the temporary form exists in the first configuration of the stent (in the folded-up state, when the stent is accommodated in the catheter tip 10) and the permanent form exists in the second configuration of the stent (in the expanded state of the stent after release of the stent from the catheter tip 10).

In the embodiments of the insertion system 100 previously described, the guiding tube 52 is preferably made from a material allowing the guiding tube 52 to be capable of traversing a tortuous pathway in the body of the patient without kinking. For example, the guiding tube 52 may include an inner lubricious liner, an outer polymeric jacket, and a coil reinforcement between the inner and outer layers. In addition, it is preferred when at least on radiopaque band or member is incorporated within the guiding tube's material to allow precise location of the distal end of the guiding tube 52 for positioning accuracy.

On the other hand, the first and second catheter tubes 32, 42 of the catheter shaft 30 are preferably made from flexible, sterilizable materials. These materials may include, for example, polyurethane, silicone, polyvinyl chloride (PVC) nylon and/or polyether block amide, e.g. Pebax®. Furthermore, the first catheter tube 32 and/or second catheter tube 42 are/is at least partly made from a less rigid material than the guiding tube 52. In an exemplary embodiment, the first catheter tube 32 and/or the second catheter tube 42 are/is at least partly made of a braided wire construction. In addition, the stent holder tube 62 may also be at least partly made of a braided wire construction.

Individual features of different embodiments of this disclosure may be combined in any suitable manner.

A preferred embodiment of a medical device for treatment of a heart valve stenosis and/or heart valve insufficiency in a patient is described in the following with reference to FIGS. 12a to 12c. As depicted, the medical device exhibits an insertion system 100 designed for transarterial/transfemoral access, as has been described in detail previously, for example, with reference to FIGS. 1 to 10.

In addition to the insertion system 100, the medical device has an expandable heart valve stent 150 mounted in the catheter tip 10 of the insertion system 100, to which a heart valve prosthesis 160 to be implanted is fastened. In the first functional state, not shown, the stent 150 exhibits a first, previously definable configuration, in which it is in its folded-together state. On the other hand, the stent 150 is designed to adopt a second previously definable configuration in the implanted state, in which it exists in its expanded state.

Through the use of the insertion system 100 described above, during the implantation procedure, the stent 150 is transferred sequentially, following a previously definable sequence of events in steps from its first previously defined configuration into its second previously defined configuration.

In detail, the stent 150 that is used with the medical device in accordance with the depiction in FIGS. 12a to 12c exhibits a first retaining region, to which the heart valve prosthesis 160 is attached. Further, the stent 150 comprises a second retaining region with three retaining elements 151, each in the configuration of retaining rings, which can be brought in to a releasable engagement with the retaining elements 16 of the stent holder 15 provided in the catheter tip 10.

In addition, the stent 150 has three retaining hoops 153 to accommodate the heart valve prosthesis 160 and three positioning hoops 154 for automatic positioning of the stent 150 at the implantation site, whereby the respective positioning hoops 154 of the stent 150 are designed in functional and structural respects to engage the pockets 170 of the native heart valve during the implantation procedure and in the implanted state of the stent 150, in particular from the second functional state of the insertion system 100. In detail, each positioning hoop 154 and its associated retaining hoop 153 has an essentially U or V-shaped structure, which is closed towards the distal end of the stent 150.

The stent 150, which together with the insertion system 100 forms the basis of the medical device, is especially suitable for insertion into the body of a patient with the aid of the insertion system 100 with minimal invasiveness. The distinctive feature of the stent 150 is that the three positioning hoops 154 of the stent 150 undertake the function of automatic positioning of the stent 150 with the heart valve prosthesis 160 attached to it in the aorta of the patient. The positioning hoops 154 have radiused head sections, which engage in the pockets 170 of the insufficient heart valve to be replaced by the heart valve prosthesis during positioning of the stent 150 at the implantation site. The provision of a total of three positioning hoops 154 takes care of the necessary positioning accuracy in the rotary direction.

In this state shown in 12a, the catheter tip 10 and the catheter shaft 30 of the transarterial or transfemoral insertion system 100 has been inserted by a puncture of the groin artery of the patient and the catheter tip 10 has been advanced to the implantation site with the aid of a guide wire 180. In detail, the insertion system 100 to be used is shown already in its second functional state in FIG. 12a. The second functional state of the insertion system 100 designed for transarterial or transfemoral access has been described previously, for example with reference to FIG. 7b.

In the second functional state, the first sleeve-shaped member 11 of the catheter tip 10 has already moved by a first predetermined amount of movement in a proximal direction, and thus towards the handle 70, leading to a release of the positioning hoops 154 of the stent 150. These already expanded positioning hoops 154 of the stent 150 shown in FIG. 12*a* are positioned—where necessary by a suitable rotation of the stent holder 15 of the catheter tip 10—in the pockets 170 of the native heart valve position. After positioning of the positioning hoops 154 in the pockets 170 of the native heart valve is complete, the insertion system 100 is transferred from its second functional state (see FIG. 7*b*) into its third functional state (see FIG. 7*c*).

The manner in which the insertion system 100 is transferred into its third functional state has been described previously, for example with reference to FIG. 7*c*. FIG. 12*b* shows the insertion system 100 in accordance with FIG. 12*a*, in which the second sleeve-shaped member 21 has been displaced in a distal direction so that the first retaining region of the stent 150 with the retaining hoops 153 and the heart valve prosthesis 160 attached to them are released. These components are opened as a result of the radial forces attacking them, whereby the old heart valves are clamped between the positioning hoops 154 and the retaining hoops 153.

After the functioning of the heart valve prosthesis 160 has been checked, the insertion system 100 is then transferred from its third functional state into its fourth functional state, as has previously been described, for example with reference to FIG. 7*d*. FIG. 12 shows the effect of the transfer of the insertion system 100 into its fourth functional state on the heart valve prosthesis 160 and the stent 150.

In detail, it can be seen that, in the fourth functional state of the insertion system 100, the first sleeve-shaped member 11 of the catheter tip 10 has been displaced further in a proximal direction, as a result of which the anchorage of the retaining elements 151 on the second retaining region of the stent 150 is released. This has the result that that the second retaining region of the stent 150 can also expand and press against the vessel wall.

Finally, the catheter tip 10 and the catheter shaft 30 of the insertion system 100 are removed again from the body of the patient.

When the heart valve stent 150 is implanted, the old (insufficient) heart valve is pressed against the vessel wall at the same time due to the self-expanding characteristic of the stent 150, as can be seen in particular in FIG. 12*c*. In particular, the semilunar heart valves of the insufficient, native heart valve are clamped between the positioning hoops 154 and the retaining hoops 153 because of the expansion of the stent 150, in addition to which the heart valve prosthesis 160 located on the first retaining region of the stent 150 is optimally positioned and is stably anchored.

The disclosed solutions provide an improved insertion system 100 with the stent mountable in the catheter tip 10 of the insertion system 100. The stent may be inserted transarterially by the special insertion system 100 and can be optimally positioned, so that a heart valve prosthesis sewn on the first retaining region of the stent can undertake the function of the insufficient or stenosed native heart valve. The radial forces developed due to the self-expanding characteristic of the stent ensure a secure anchoring in the area of the aorta. The catheter system 1 of the insertion system 100 is preferably an 18 to 21F introducer, which is compatible with 21F-insertion tubes and a 0.035" guide wire 180. The length of the catheter system 1 for transarterial access should be at least 100 cm. The optionally provided flexural link region at the distal region of the catheter system 1 is preferably approximately 30 cm.

A further embodiment of a catheter tip 10 for an insertion system for transfemoral/transarterial insertion of an expandable heart valve stent is shown in its four different functional states in FIGS. 13*a* to 13*d*. In detail, the catheter tip 10 is shown in its first functional state in FIG. 13*a*, in which the catheter shaft with the catheter tip 10 and, where required, with the stent accommodated in it can be inserted into the patient transarterially or transfemorally and advanced via the aorta to the implantation site.

In the first functional state of the catheter tip 10 in accordance with FIG. 13*a*, the catheter tip 10 is completely closed, whereby the two sleeve-shaped members 11, 21 of the catheter tip 10 abut. In this embodiment, the two sleeve-shaped members 11, 21 of the catheter tip 10 have an equal outer cross-section diameter, thereby not forming a step in the state depicted in FIG. 13*a*. The respective inner diameters of the sleeve-shaped members 11, 21 are chosen so that the folded-up retaining hoops of a stent, with the heart valve prosthesis fastened to them where required, can be housed in the second sleeve-shaped member 21. The folded-up positioning hoops of the stent housed between the second sleeve-shaped member 21 and the first sleeve-shaped member 11 are held together in their folded form.

In the first functional state of the catheter tip 10, as shown in FIG. 13*a*, the second retaining region of the stent is fixed with the stent holder 15 at the proximal end of the catheter tip 10. For this purpose, the retaining elements (retaining rings etc.) provided at the second retaining region of the stent are engaged with retaining elements 16 of the stent holder 15.

The retaining elements 16 of the stent holder 15 are covered by the first sleeve-shaped member 11 of the catheter tip 10 in the first functional state shown in FIG. 13*a*, so that an engagement between retaining elements provided on the second retaining region of a stent and retaining elements 16 of the stent holder 15 would be possible.

The first functional state of the catheter tip 10 shown in FIG. 13*a* is maintained during the transarterial insertion procedure. On reaching the implantation location, the catheter tip 10 is transferred from the first functional state shown in FIG. 13*a* to the second functional state shown in FIG. 13*b*, by transferring the first operating means of the handle (first operating means 71 shown in the embodiment of the wheel in FIG. 7) from the first position into the second position. The longitudinal displacement stroke transferred by actuation of the first operating means 71 to the first sleeve-shaped member 11 of the catheter tip 10 effects a displacement of the first sleeve-shaped member 11 relative to the stent holder 15 in the proximal direction, thus towards the handle 70.

The longitudinal displacement stroke executed on the first sleeve-shaped member 11 of the catheter tip 10 during the transition from the first functional state (see FIG. 13*a*) to the second functional state (see FIG. 13*b*) by the first operating means 71 of the handle 70 via a corresponding first force transmission means 31 is previously defined so that the first sleeve-shaped member 11 is displaced relative to the stent holder 15 in the proximal direction just so far that the positioning hoops of a stent housed in the catheter tip 10 would be released, though the distal end of the first sleeve-shaped member 11 of the catheter tip 10 would still cover the retaining elements 16 of the stent holder 15, so that the engagement between the retaining elements provided at the second retaining region of the stent and the retaining elements 16 of the stent holder 15 would be secure.

Since the second sleeve-shaped member 21 is not manipulated during the transition from the first functional state into the second functional state, the first retaining region of a stent housed in the catheter tip 10 with the heart valve prosthesis fastened to it would continue to be housed in its folded together state in the sleeve-shaped element of the second sleeve-shaped member 21.

The positioning hoops of a stent housed in the catheter tip 10 released in the second functional state of the catheter tip 10 are opened as a result of the radial forces acting on them and can thus be positioned in the pockets of the insufficient native heart valve. Following appropriate positioning of the positioning hoops of the stent in the pockets of the native heart valve, the catheter tip 10 is transferred from the second functional state shown in FIG. 13*b* into the third functional state shown in FIG. 13*c*. This is done my manipulation of the second operating means 81 of the handle, after the securing element 89 associated with the second operating means 81 has been removed.

On actuation of the second operating means 81 of the handle, the second sleeve-shaped member 21 of the catheter tip 10 associated with the second operating means 81 is moved relative to the stent holder 15 by a previously established longitudinal displacement stroke defined with the second operating means 81 in a distal direction, thus away from the handle 70. The longitudinal displacement stroke acting on the second sleeve-shaped member 21 is chosen so that the sleeve-shaped member 21 no longer covers the first retaining region of a stent housed in the catheter tip 10 with the heart valve prosthesis fastened to it, where required, and thus releases the first retaining region of the stent. Due to the action of the radial forces, the distal retaining region of the stent with the heart valve prosthesis attached to it, where required, unfolds completely.

Since the first operating means 71 of the handle 70 and the associated first sleeve-shaped member 11 of the catheter tip 10 are not manipulated during the transition from the second functional state in accordance with FIG. 13*b* into the third functional state in accordance with FIG. 13*c*, the distal end region of the first sleeve-shaped member 11 continues to cover the retaining elements 16 of the stent holder 15, so that the engagement between the retaining elements of a stent housed in the catheter tip 10 and the retaining elements 16 of the stent holder 15 is secure and the proximal retaining region of the stent is in its folded-up state. This anchorage of the stent to the catheter tip 10 of the insertion system 100 allows an explantation of a stent that is already partially unfolded by returning the catheter tip 10 from the third functional state, by appropriate manipulation of the second operating means 81 of the handle 70, to the second functional state and then by suitable actuation of the first operating means 71 transfer to the first functional state.

If an explantation of the stent with the heart valve prosthesis attached to it, where required, is unnecessary, the catheter tip 10 is transferred from the third functional state shown in FIG. 13*c* into the fourth functional state shown in FIG. 13*d*, by turning the first operating means 71 of the handle 70 further from the second position to the third position after removal of the securing element 79 (locking element). This manipulation of the first operating means 71 that can be effected after removal of the securing element 79 results in a further defined movement of the first sleeve-shaped member 11 relative to the stent holder 15 of the catheter tip 10 in a proximal direction, thus towards the handle 70. The longitudinal displacement stroke executed on the first sleeve-shaped member 11 is chosen so that the distal end of the first sleeve-shaped member 11 no longer covers the retaining elements 16 of the stent holder 15, as a result of which an engagement between the retaining elements of a stent housed in the catheter tip 10 and the retaining elements 16 of the stent holder 15 can be released, which would also lead to a complete release of the second retaining region of the stent and a complete separation of the stent from the catheter tip 10 and correspondingly to a complete unfolding of the stent.

In the embodiment of the catheter tip 10 depicted in FIGS. 13*a-e*, a stent holder tube 62 is used for connecting the stent holder 15 of the catheter tip 10 to the body 70' of the handle 70. The stent holder tube 62 has a distal end connected to the stent holder 15, a proximal end connected to the body 70' of the handle 70 and a passageway extending through the stent holder tube 62. In addition, an extension portion 62' of the stent holder tube 62 is provided, said extension portion extending from the distal end of the stent holder 15 to a support section 63. The support section 63 may be a tapered portion which is completely accommodated in the second sleeve-shaped member 21 when the catheter tip 10 is in its first and second functional state (cf. FIGS. 13*a, b*).

Preferably, the stent holder tube 62 and its extension 62' have a cross-section less than the cross-section of the first catheter tube 32 and greater than the cross-section of the second catheter tube 42 (not shown in FIGS. 13*a-e*), wherein the first catheter tube 32 is disposed concentrically and coaxially with the stent holder tube 62 thereby accommodating the stent holder tube 62 such that the first catheter tube 32 is moveable relative to the stent holder tube 62. The passageway of the stent holder tube 62 shall have a diameter sufficient to accommodate the second catheter tube 42 such that the second catheter tube 42 is moveable relative to the stent holder tube 62.

FIG. 13*e* shows a side elevation of the embodiment of the catheter tip 10 in accordance with FIG. 13*a-d*, whereby the catheter tip 10 is in its state after releasing a stent housed in the catheter tip 10 and ready to be removed again from the body of the patient. In this state of the catheter tip 10, the first sleeve-shaped member 11 is pushed by manipulation of the first operating means 71 of the handle 70 such that the first sleeve-shaped member 11 is in its most distal position, in which the distal end of the first sleeve-shaped member 11 abuts against the proximal end of the second sleeve-shaped member 21 without any gap or step there between. For securing this gap and step free state, the distal end of the first sleeve-shaped members 11 is supported by the already mentioned support section 63.

The disclosed solution is not limited to the preferred embodiment described in the attached drawings. On the contrary, combinations of the individual features described in detail are also possible.

| | List of reference numerals |
|---|---|
| 1 | catheter system |
| 10 | catheter tip |
| 11 | first sleeve-shaped member |
| 15 | stent holder |
| 16 | retaining elements |
| 21 | second sleeve-shaped member |
| 25 | catheter end tip |
| 30 | catheter shaft |
| 31 | first force transmission means |
| 32 | first catheter tube |
| 34 | flexural link region |
| 36 | channel |
| 35 | control wire |
| 40 | filler body |
| 41 | second force transmission means |
| 42 | second catheter tube |
| 43 | fluid channels |
| 51 | guiding means |

-continued

List of reference numerals

| | |
|---|---|
| 52 | guiding tube |
| 53 | inlet port |
| 62 | stent holder tube |
| 62' | extension of stent holder tube |
| 63 | support means |
| 70 | handle |
| 70' | body of the handle |
| 71 | first operating means |
| 72 | first guide |
| 73 | first pusher |
| 74 | first slide |
| 74' | screw cap |
| 75 | first stop |
| 76 | second stop |
| 77 | additional stop |
| 77' | locking element |
| 79 | securing element |
| 81 | second operating means |
| 82 | second guide |
| 83 | second pusher |
| 84 | second slide |
| 85 | first stop |
| 86 | second stop |
| 87 | fixing |
| 88 | grip |
| 89 | securing element |
| 96 | third operating means |
| 97 | compression spring |
| 97a | first stop |
| 97b | second stop |
| 98 | turning mechanism/rotatable cap |
| 99a | first injection adapter |
| 99b | second injection adapter |
| 100 | insertion system |
| 150 | stent |
| 151 | retaining elements |
| 153 | retaining hoops |
| 154 | positioning hoops |
| 160 | heart valve prosthesis |
| 170 | pockets of native heart valve |
| 180 | guiding wire |
| L | longitudinal direction of insertion system 100 |

The invention claimed is:

1. A method of implanting an endoprosthesis including three positioning arches, three retaining arches, a valve prosthesis directly attached to the three retaining arches, and a plurality of retaining elements, the method comprising:
positioning the endoprosthesis relative a native heart valve;
manipulating a handle of a catheter to move a first sleeve with respect to a stent holder in a first direction toward the handle to uncover the positioning arches while covering the plurality of retaining elements within the first sleeve, wherein manipulating the handle moves a first tubular member coupled to the first sleeve in the first direction;
positioning the positioning arches within pockets of the native valve;
manipulating the handle to move a second sleeve with respect to the stent holder in a second direction opposite the first direction and away from the handle to uncover the retaining arches, wherein manipulating the handle moves a second tubular member coupled to the second sleeve in the second direction; and
securing a plurality of native leaflets of the native valve within the positioning arches and outside of the retaining arches;
wherein the stent holder is fixed relative to the handle via a holder tube extending proximally from the stent holder, the holder tube having a distal end connected to the holder and a proximal end connected to the handle, and wherein the holder tube is within the first tubular member, and
wherein the holder includes a holder support section distal to the holder, and an extension portion has a proximal end connected to the holder and a distal end connected to the holder support section.

2. The method of claim 1, wherein the step of manipulating the handle to move the second sleeve relative the stent holder to uncover the retaining arches allows the retaining arches and the valve prosthesis to expand, wherein each of the three retaining arches includes an apex axially aligned along a longitudinal direction of the endoprosthesis with a respective apex of one of the three positioning arches.

3. The method of claim 1, wherein the second tubular member is disposed within the first tubular member.

4. The method of claim 3, wherein the holder tube and the extension portion each has an outer cross-section diameter less than an outer cross-section of the first tubular member and greater than an outer cross-section diameter of the second tubular member, wherein the holder tube is disposed within the first and second tubular members.

5. The method of claim 1, wherein the endoprosthesis overlies the holder, the extension portion, and the holder support section when the endoprosthesis is in a collapsed configuration, and wherein the three positioning arches includes exactly three positioning arches, and the three retaining arches includes exactly three retaining arches.

6. The method claim 1, wherein the holder support section includes a tapered portion completely accommodated in the second sleeve when manipulating the handle to move the second tubular member in the second direction.

7. The method of claim 1, further comprising moving the first sleeve in the first direction to uncover the plurality of retaining elements.

8. A method of implanting an endoprosthesis including a plurality of positioning arches, a plurality of retaining arches, a valve prosthesis directly attached to each of the retaining arches, and a plurality of retaining elements, the method comprising:
positioning the endoprosthesis relative a native valve;
manipulating a handle of a catheter to move a first sleeve relative to a stent holder in a first direction to uncover the positioning arches while covering the plurality of retaining elements, wherein the first sleeve at least partially surrounds the stent holder;
positioning the positioning arches within pockets of the native valve;
manipulating the handle to move a second sleeve in a second direction opposite the first direction to uncover the retaining arches to allow the retaining arches and the valve prosthesis to expand, wherein each of the retaining arches includes an apex axially aligned with an apex of a corresponding positioning arch;
securing a plurality of leaflets of the native valve within the positioning arches and outside of the retaining arches; and
manipulating the handle to further move the first sleeve to uncover the plurality of retaining elements;
wherein the stent holder is fixed relative to the handle via a holder tube extending proximally from the stent holder, the holder tube having a distal end connected to the holder and a proximal end connected to the handle, and wherein the holder tube is within the first tubular member, and wherein the holder includes a holder support section distal to the holder, and an extension portion has a proximal end connected to the holder and a distal end connected to the holder support section.

9. The method of claim 8, wherein the plurality of positioning arches includes exactly three positioning arches, and the plurality of retaining arches includes exactly three retaining arches.

10. The method of claim 8, wherein manipulating the handle to move the first sleeve includes rotation of a portion of the handle to move a first tubular member coupled to the first sleeve in the first direction; and wherein manipulating the handle to move the second sleeve includes moving a second tubular member coupled to the second sleeve in the second direction.

11. The method of claim 10, wherein the second tubular member is disposed within the first tubular member.

12. The method of claim 11, wherein the holder tube and the extension portion each has an outer cross-section diameter less than an outer cross-section of the first tubular member and greater than an outer cross-section diameter of the second tubular member, wherein the holder tube is disposed within the first and second tubular members.

13. The method of claim 8, wherein the endoprosthesis overlies the holder, the extension portion, and the holder support section when the endoprosthesis is in a collapsed configuration.

14. The method claim 8, wherein the holder support section includes a tapered portion completely seated in the second sleeve when manipulating the handle of the catheter to uncover the positioning arches while covering the plurality of retaining elements.

15. A method of implanting an endoprosthesis including exactly three positioning arches, exactly three retaining arches, a valve prosthesis directly attached to each of the exactly three retaining arches, and a plurality of retaining elements, the method comprising:
  positioning the endoprosthesis relative a native heart valve;
  rotating a handle of a catheter about a first tubular member to move a first sleeve with respect to a stent holder in a first direction toward the handle to uncover the positioning arches while covering the plurality of retaining elements within the first sleeve, wherein the first tubular member is coupled to the first sleeve;
  positioning the positioning arches within pockets of the native valve;
  actuating the handle to move a second sleeve with respect to the stent holder in a second direction, opposite the first direction, and away from the handle to uncover the retaining arches, wherein manipulating the handle includes moving a second tubular member coupled to the second sleeve in the second direction; and
  securing a plurality of native leaflets of the native valve within the positioning arches and outside of the retaining arches;
  wherein the stent holder is fixed relative to the handle via a holder tube extending proximally from the stent holder, the holder tube having a distal end connected to the holder and a proximal end connected to the handle, and wherein the holder tube is within the first tubular member, and
  wherein the holder includes a holder support section distal to the holder, and an extension portion has a proximal end connected to the holder and a distal end connected to the holder support section.

16. The method of claim 15, further comprising moving the endoprosthesis through an aortic arch before positioning the endoprosthesis relative to the native valve.

17. The method of claim 15, wherein the step of actuating the handle to move the second sleeve relative the stent holder to uncover the retaining arches allows the retaining arches and the valve prosthesis to expand, wherein each of the three retaining arches includes an apex axially aligned along a longitudinal direction of the endoprosthesis with a respective apex of one of the three positioning arches.

18. The method of claim 15, wherein the holder tube and the extension portion each has an outer cross-section diameter less than an outer cross-section of the first tubular member and greater than an outer cross-section diameter of the second tubular member, wherein the holder tube is disposed within the first and second tubular members.

19. The method claim 15, wherein the holder support section is tapered.

20. The method of claim 15, wherein the positioning arches, the retaining arches, the valve prosthesis, and the plurality of retaining elements are held in a collapsed state within a tip of the catheter by the first and second sleeves.

* * * * *